United States Patent

Kierstead et al.

[11] 4,348,396
[45] Sep. 7, 1982

[54] SUBSTITUTED 11-OXO-11H-PYRIDO[2,1-B]QUINAZOLINES AND METHOD OF INHIBITING ALLERGIC REACTIONS WITH THEM

[75] Inventors: Richard W. Kierstead; Jefferson W. Tilley, both of North Caldwell, N.J.

[73] Assignee: Hoffmann-La Roche Inc., Nutley, N.J.

[21] Appl. No.: 146,730

[22] Filed: May 2, 1980

Related U.S. Application Data

[63] Continuation of Ser. No. 871,564, Jan. 23, 1978, abandoned, which is a continuation-in-part of Ser. No. 780,939, Mar. 24, 1977, abandoned.

[51] Int. Cl.³ .................. A61K 31/505; C07D 471/04
[52] U.S. Cl. ..................................... 424/251; 544/252
[58] Field of Search ......................... 544/252; 424/251

[56] References Cited

U.S. PATENT DOCUMENTS

| | | | |
|---|---|---|---|
| 3,966,965 | 6/1976 | Sellstedt et al. | 424/309 |
| 3,982,000 | 9/1976 | Hardtmann | 424/251 |
| 4,012,387 | 3/1977 | Schwender et al. | 544/252 |
| 4,033,961 | 7/1977 | Schwender et al. | 544/252 |
| 4,066,767 | 1/1978 | Schwender et al. | 424/251 |
| 4,083,980 | 4/1978 | Schromm et al. | 424/251 |
| 4,104,389 | 8/1978 | Schwender et al. | 424/251 |
| 4,220,771 | 9/1980 | Hermecz et al. | 544/252 |

FOREIGN PATENT DOCUMENTS 2739020  3/1979 Fed. Rep. of Germany ...... 544/252
6414717  6/1965 Netherlands .

*Primary Examiner*—Donald G. Daus
*Assistant Examiner*—Diana G. Rivers
*Attorney, Agent, or Firm*—Jon S. Saxe; Bernard S. Leon; William G. Isgro

[57] ABSTRACT

Pyrido[2,1-b]quinazolines of the formulas

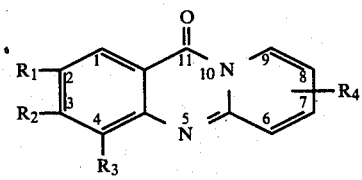

and

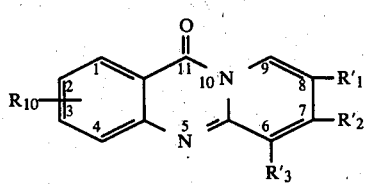

wherein $R_1$, $R_1'$, $R_2$, $R_2'$, $R_3$, $R_3'$, $R_4$ and $R_{10}$ are as hereinafter set forth, and processes for the preparation thereof, are described. The compounds of formulas I and II are useful as agents in the prevention of allergic reactions.

35 Claims, No Drawings

SUBSTITUTED 11-OXO-11H-PYRIDO[2,1-B]QUINAZOLINES AND METHOD OF INHIBITING ALLERGIC REACTIONS WITH THEM

CROSS-REFERENCE TO RELATED APPLICATIONS

This is a continuation, of application Ser. No. 871,564, filed Jan. 23, 1978, which is a continuation-in-part of U.S. Patent Application Ser. No. 780,939, filed Mar. 24, 1977, both abandoned.

BRIEF SUMMARY OF THE INVENTION

The invention relates to compounds of the formula

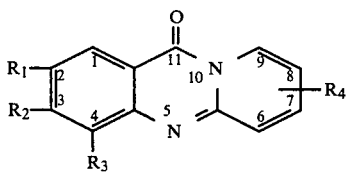
I wherein $R_1$, $R_2$ and $R_3$, independently, are hydrogen, lower alkyl, lower alkoxy, lower alkylthio, halogen, cyclopropyl, cyclobutyl, or hydroxy; and $R_4$ is cyano, 5-tetrazolyl, hydroxy-lower alkyl, acyloxylower alkyl or a radical of the formula

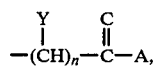

wherein A is lower alkyl, hydroxy, lower alkoxy, di-($C_1$–$C_7$)alkylamino-($C_2$–$C_7$)-alkoxy, pivaloyloxymethoxy, or a radical of the formula

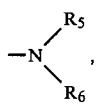

wherein $R_5$ and $R_6$, independently, are hydrogen, lower alkyl or di-($C_1$–$C_7$)alkylamino-($C_2$–$C_7$)alkyl, Y is hydrogen or methyl, and n is 0 or 1; provided that at least one of $R_1$, $R_2$ and $R_3$ is other than hydrogen and that $R_4$ is present only in position 6, 7 or 8, or a pharmaceutically acceptable acid addition salt thereof, or when A is hydroxy, also a salt thereof with a pharmaceutically acceptable base.

In another aspect, the invention relates to compounds of the formula

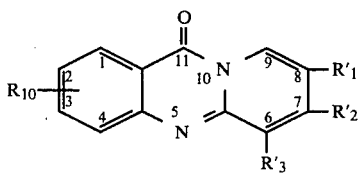
II wherein $R_{10}$ is cyano, 5-tetrazolyl, halogen, or a radical of the formula

wherein A is hydroxy, lower alkoxy, di-($C_1$–$C_7$)alkylamino-($C_2$–$C_7$)alkoxy, pivaloyloxymethoxy or

wherein $R_5$ and $R_6$, independently, are hydrogen, lower alkyl or di-($C_1$–$C_7$)-alkylamino-($C_2$–$C_7$)alkyl, and $R_1'$, $R_2'$ and $R_3'$, independently, are hydrogen, lower alkanoyl, or lower alkyl; provided that $R_{10}$ is a substituent only in position 2, 3 or 4, and provided that it is other than halogen when $R_1'$, $R_2'$ or $R_3'$ is lower alkanoyl, or a pharmaceutically acceptable acid addition salt thereof, or when A is hydroxy, also a salt thereof with a pharmaceutically acceptable base.

The compounds of formulas I and II are useful in the prevention of allergic reactions, for example, they are useful in the prophylactic treatment of bronchial asthma.

DETAILED DESCRIPTION OF THE INVENTION

The invention relates to substituted 11-oxo-1H-pyrido[2,1-b] quinazolines of the formula

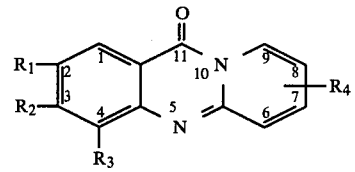
I wherein $R_1$, $R_2$ and $R_3$, independently, are hydrogen, lower alkyl, lower alkoxy, lower alkylthio, halogen, cyclopropyl, cyclobutyl or hydroxy; and $R_4$ is cyano, 5-tetrazolyl, hydroxy-lower alkyl, acyloxy-lower alkyl or a radical of the formula

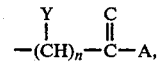

wherein A is lower alkyl, hydroxy, lower alkoxy, di-($C_1$–$C_7$)alkylamino-($C_2$–$C_7$)alkoxy, pivaloyloxymethoxy, or a radical of the formula

wherein $R_5$ and $R_6$, independently, are hydrogen, lower alkyl or di-($C_1$–$C_7$)alkylamino-($C_2$–$C_7$)alkyl, Y is hydrogen or methyl, and n is 0 or 1; provided that at least one of $R_1$, $R_2$ and $R_3$ is other than hydrogen and that $R_4$ is present only in position 6, 7 or 8, or a pharmaceutically acceptable acid addition salt thereof, or when A is hydroxy, also a salt thereof with a pharmaceutically acceptable base, and 11-oxo-11H-pyrido[2,1-b] quinazolines of the formula

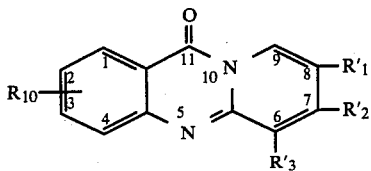

II wherein $R_{10}$ is cyano, 5-tetrazolyl, halogen, or a radical of the formula

wherein A is hydroxy, lower alkoxy, di($C_1$–$C_7$)alkylamino-($C_2$–$C_7$)alkoxy, pivaloyloxymethoxy or

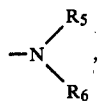

wherein $R_5$ and $R_6$, independently, are hydrogen, lower alkyl or di-($C_1$–$C_7$)alkylamino-($C_2$–$C_7$)alkyl, and $R_1'$, $R_2'$ and $R_3'$, independently, are hydrogen, lower alkanoyl or lower alkyl; provided that $R_{10}$ is a substituent only in position 2, 3 or 4, and provided that $R_{10}$ is other than halogen when $R_1'$, $R_2'$ or $R_3'$ is lower alkanoyl, or a pharmaceutically acceptable acid addition salt thereof, or when A is hydroxy, also a salt thereof with a pharmaceutically acceptable base.

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "lower alkoxy" denotes an alkoxy group in which the lower alkyl group is as described above, for example, methoxy, ethoxy, propoxy, pentoxy, and the like. The term "halogen" denotes all the halogens, i.e., bromine, chlorine, fluorine, and iodine. The term "acyl" denotes an "alkanoyl" group derived from an aliphatic carboxylic acid of 1 to 7 carbon atoms, for example, formyl, acetyl, propionyl, and the like; and an "aroyl" group derived from an aromatic carboxylic acid, such as benzoyl and the like. The term "acyloxy" denotes an "alkanoyloxy" group derived from an aliphatic carboxylic acid of 1 to 7 carbon atoms, for example, formyloxy, acetoxy, propionyloxy, and the like; and an "aroyloxy" group derived from an aromatic carboxylic acid, such as benzoyloxy and the like. Exemplary of "di-($C_1$–$C_7$)alkylamino-($C_2$–$C_7$)alkoxy" groups are dimethylaminoethoxy, diethylaminoethoxy, dipropylaminoethoxy, diisopropylaminoethoxy, dibutylaminoethoxy, dipentylaminoethoxy, or the like. Exemplary of "di-($C_1$–$C_7$)alkylamino-($C_2$–$C_7$)alkyl" groups are dimethylaminoethyl, diethylaminoethyl, ethylmethylaminoethyl, dipropylaminoethyl, or the like. Exemplary of "acyloxy-lower alkyl" groups are formyloxymethyl, acetyloxymethyl, propionyloxymethyl, benzoyloxymethyl, or the like.

In a preferred aspect, the invention comprises compounds of formula I wherein at least one of $R_1$, $R_2$ and $R_3$ is lower alkyl, lower alkoxy or lower alkylthio, and $R_4$ is a substituent in position 8. In a more preferred aspect, the invention comprises compounds of formula I wherein $R_2$ is hydrogen, $R_1$ and/or $R_3$ are other than hydrogen, and $R_4$ is a substituent in position 8. Still more preferred are compounds of formula I wherein $R_2$ is hydrogen; $R_1$ and/or $R_3$, independently, are lower alkyl, lower alkoxy or lower alkylthio; and $R_4$ is hydroxy-lower alkyl, 5-tetrazolyl, or

wherein A is hydroxy or di-($C_1$–$C_7$)alkylamino-($C_2$–$C_7$)alkoxy. Most preferred are compounds of formula I, wherein one of $R_1$, $R_2$ or $R_3$ is lower alkyl, lower alkoxy or lower alkylthio and $R_4$ is

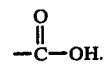

Preferred compounds of formula I are the following:
2-methoxy-11-oxo-11H-pyrido[2,1-b]quinazoline-8-carboxylic acid;
2-thiomethyl-11-oxo-11H-pyrido[2,1-b]quinazoline-8-carboxylic acid; and
2-isopropyl-11-oxo-11H-pyrido[2,1-b]quinazoline-8-carboxylic acid.

Preferred compounds of formula II are the following:
8-methyl-11-oxo-11H-pyrido[2,1-b]quinazoline-2-carboxylic acid;
8-ethyl-11-oxo-11H-pyrido[2,1-b]quinazoline-2-carboxylic acid; and
8-isopropyl-11-oxo-11H-pyrido[2,1-b]quinazoline-2-carboxylic acid.

Exemplary of the compounds of formula I are the following:
4-isopropyl-11-oxo-11H-pyrido[2,1-b]quinazoline-8-carboxylic acid;
4-isopropoxy-11-oxo-11H-pyrido[2,1-b]quinazoline-8-carboxylic acid;
4-methylthio-11-oxo-11H-pyrido[2,1-b]quinazoline-8-carboxylic acid;
2,4-diisopropyl-11-oxo-11H-pyrido[2,1-b]quinazoline-8-carboxylic acid;
2,4-diisopropoxy-11-oxo-11H-pyrido[2,1-b]quinazoline-8-carboxylic acid;
2,4-dimethylthio-11-oxo-11H-pyrido[2,1-b]quinazoline-8-carboxylic acid;
11-oxo-11H-pyrido[2,1-b]quinazoline-8-acetic acid;
2-chloro-11-oxo-11H-pyrido[2,1-b]quinazoline-8-acetic acid;
3-methoxy-11-oxo-11H-pyrido[2,1-b]quinazoline-8-acetic acid;
3-chloro-11-oxo-11H-pyrido[2,1-b]quinazoline-8-acetic acid;
2-methoxy-11-oxo-11H-pyrido[2,1-b]quinazoline-7-acetic acid;
2-chloro-11-oxo-11H-pyrido[2,1-b]quinazoline-7-acetic acid;
2-methoxy-11-oxo-11H-pyrido[2,1-b]quinazoline-8-α-methylacetic acid;
2-chloro-11-oxo-11H-pyrido[2,1-b]quinazoline-8-α-methylacetic acid;
3-methoxy-11-oxo-11H-pyrido[2,1-b]quinazoline-8-α-methylacetic acid;
3-chloro-11-oxo-11H-pyrido[2,1-b]quinazoline-8-α-methylacetic acid;
2-methoxy-11-oxo-11H-pyrido[2,1-b]quinazoline-7-α-methylacetic acid;

2-chloro-11-oxo-11H-pyrido[2,1-b]quinazoline-7-α-methylacetic acid;
2-isopropyl-11-oxo-11H-pyrido[2,1-b]quinazoline-8-carboxylic acid (2-diethylaminoethyl) ester hydrochloride;
2-methylthio-11-oxo-11H-pyrido[2,1-b]quinazoline-8-carboxylic acid (2-diethylaminoethyl) ester hydrochloride;
2-isopropylthio-11-oxo-11H-pyrido[2,1-b]quinazoline-8-carboxylic acid (2-diethylamino-ethyl) ester hydrochloride;
2-isopropyl-11-oxo-11H-8(1H-tetrazol-5-yl)pyrido[2,1-b]quinazoline;
2-isopropoxy-11-oxo-11H-8(1H-tetrazol-5-yl)pyrido[2,1-b]quinazoline;
2-cyclopropyl-11-oxo-11H-pyrido[2,1-b]quinazoline-8-carboxylic acid;
2-cyclobutyl-11-oxo-11H-pyrido[2,1-b]quinazoline-8-carboxylic acid;
2-methylthio-11-oxo-11H-8-(1H-tetrazol-5-yl)pyrido[2,1-b]quinazoline;
2-isopropylthio-11-oxo-11H-8-(1H-tetrazol-5-yl)pyrido[2,1-b]quinazoline;
8-hydroxymethyl-2-isopropyl-11H-pyrido[2,1-b]quinazoline-11-one;
8-hydroxymethyl-2-isopropyl-11H-pyrido[2,1-b]quinazoline-11-one;
8-hydroxymethyl-2-methylthio-11H-pyrido[2,1-b]quinazoline-11-one;
8-hydroxymethyl-2-isopropylthio-11H-pyrido[2,1-b]quinazoline-11-one; or the like, including compounds hereinafter set forth.

Exemplary of the compounds of formula II are the following:
8-ethyl-11-oxo-11H-pyrido[2,1-b]quinazoline-2-carboxylic acid;
8-n-propyl-11-oxo-11H-pyrido[2,1-b]quinazoline-2-carboxylic acid;
8-isopropyl-11-oxo-11H-pyrido[2,1-b]quinazoline-2-carboxylic acid;
8-n-butyl-11-oxo-11H-pyrido[2,1-b]quinazoline-2-carboxylic acid;
8-t-butyl-11-oxo-11H-pyrido[2,1-b]quinazoline-2-carboxylic acid;
6-methyl-11-oxo-11H-pyrido[2,1-b]quinazoline-2-carboxylic acid;
6-ethyl-11-oxo-11H-pyrido[2,1-b]quinazoline-2-carboxylic acid;
6-n-propyl-11-oxo-11H-pyrido[2,1-b]quinazoline-2-carboxylic acid;
6-n-butyl-11-oxo-11H-pyrido[2,1-b]quinazoline-2-carboxylic acid;
6-t-butyl-11-oxo-11H-pyrido[2,1-b]quinazoline-2-carboxylic acid; or the like, including compounds hereinafter set forth.

The compounds of formulas I and II of the invention can be prepared as hereinafter described in Schemes I, II and III.

SCHEME I

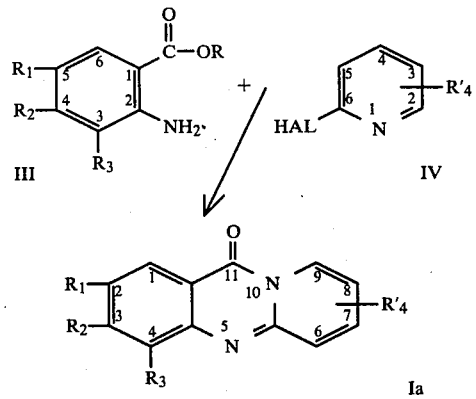

-continued

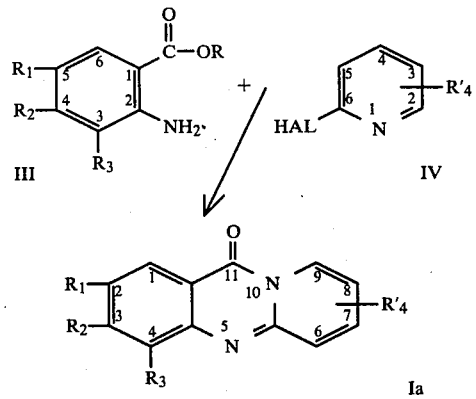

wherein R is hydrogen or lower alkyl; $R_1$, $R_2$ and $R_3$, independently, are hydrogen, lower alkyl, lower alkoxy, lower alkylthio, halogen, cyclopropyl, cyclobutyl or hydroxy; HAL is halogen; and $R_4'$ is cyano, acyloxy-lower alkyl or a radical of the formula

wherein $A'$ is lower alkyl, hydroxy, lower alkoxy, or a radical of the formula

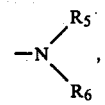

wherein $R_5$ and $R_6$, independently, are hydrogen, lower alkyl or di-$(C_1-C_7)$alkylamino-$(C_2-C_7)$alkyl, Y is hydrogen or methyl, and n is 0 or 1; provided that in formula IV $R_4'$ is a substituent only in position 3, 4 or 5, and in formula Ia $R_4'$ is a substituent only in position 6, 7 or 8, and provided that at least one of $R_1$, $R_2$ and $R_3$ is other than hydrogen.

In Scheme I, an anthranilic acid or ester of formula III, a known compound or a compound which can be prepared according to known procedures, is reacted with a halopyridine of formula IV, which is a known compound or can be prepared according to known procedures, at a temperature in the range of from about 100° C. to about 200° C., with or without a solvent. The reaction is conducted in the presence of a catalytic amount of an alkali metal iodide, such as sodium iodide, potassium iodide, cesium iodide, or the like. Solvents which may be utilized in the reaction are high boiling solvents such as acetic acid, diglyme, triglyme, or the like. The reaction is conveniently carried out at atmospheric pressure. The reaction product, i.e., a compound of formula Ia, can be recovered according to known procedures, such as crystallization, or the like.

A compound of formula I wherein $R_4$ is 5-tetrazolyl can be prepared from the corresponding compound of formula Ia wherein $R_4'$ is cyano. More specifically, the corresponding compound of formula Ia wherein $R_4'$ is cyano is treated with an alkali metal azide, such as potassium azide, sodium azide, or the like, in the presence of ammonium chloride. The reaction is suitably carried out in the presence of a solvent such as a polar aprotic solvent, for example, dimethylsulfoxide, dimethylformamide, or the like. The desired tetrazolyl compound is then recovered according to known procedures, for example, crystallization, or the like.

A compound of formula I wherein A is pivaloyloxymethoxy can be prepared from the corresponding compound of formula Ia wherein A' is hydroxy, by treating said compound with a tri-lower alkylamine and chloromethyl pivalate in an inert solvent such as dimethylformamide or the like, at a temperature in the range of room temperature to about 120° C. The desired end product can be recovered according to known procedures, such as crystallization.

A compound of formula I wherein A is di-$(C_1$-$C_7)$alkylamino-$(C_2$-$C_7)$alkoxy, can be prepared from the corresponding compound of formula Ia wherein A' is hydroxy, by treating said compound, for instance, with a di-$(C_1$-$C_7)$alkylamino-$(C_2$-$C_3)$alkyl halide under reflux conditions in a solvent, for example, an alkanol such as isopropanol or the like, and recovering the product according to known procedures, such as crystallization or the like; or treating said compound with thionyl chloride whereby the corresponding acid chloride is obtained, the latter compound is reacted with a di-$(C_1$-$C_7)$alkylamino-$(C_2$-$C_7)$alkanol in an inert solvent, such as tetrahydrofuran or the like, at a temperature in the range of from about 0° C. to about 100° C., and thereafter the desired end product is recovered by known procedures, such as crystallization or the like.

SCHEME II

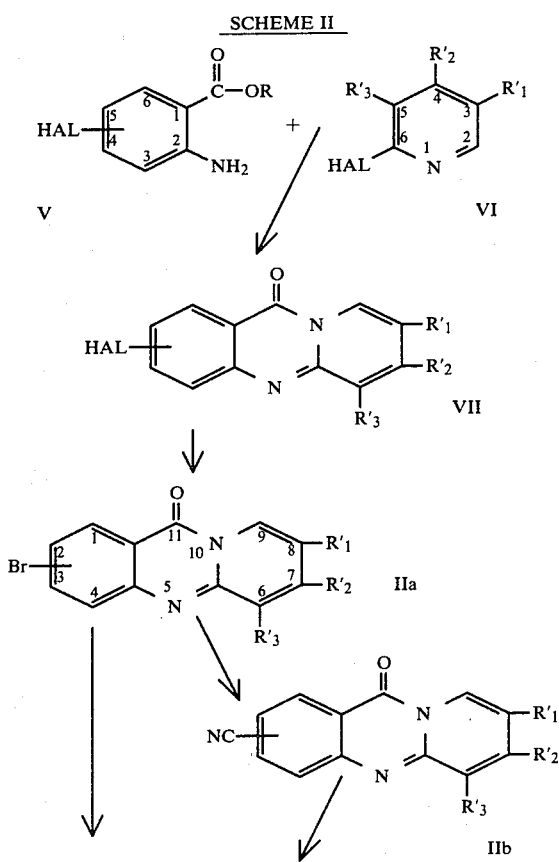

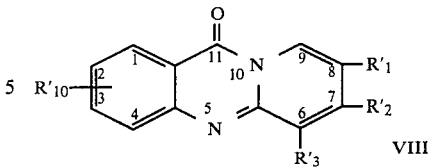

wherein R and HAL are as previously described; and $R_1'$, $R_2'$ and $R_3'$, independently, are hydrogen, lower alkanoyl or lower alkyl; provided that in formula V Br is a substituent only in position 3, 4 or 5, and that in formula IIa and formula IIb Br and CN, respectively, are substituents only in position 2, 3 or 4; $R_{10}'$ is

and is a substituent only in position 2, 3 or 4.

In Scheme II, an anthranilic acid or ester of formula V, a known compound or a compound which can be prepared according to known procedures, is reacted with a halopyridine of formula IV, a known compound or a compound which can be prepared according to known procedures, as described in Scheme I to yield a compound of formula VII. When HAL in formula VII is bromine, i.e., the compound of formula IIa, it can be converted to a compound of formula VII by treating the compound of formula IIa with nickel carbonyl in the presence of an alkaline earth hydroxide, such as calcium hydroxide, under pressure and in an atmosphere of carbon monoxide at a temperature in the range of 100° C. to about 150° C. The reaction conveniently can be carried out in a high boiling polar solvent such as dimethylformamide or the like. A compound of formula VIII can be recovered according to known procedures, such as crystallization or the like. The bromo moiety of a compound of formula IIa can be converted to a nitrile moiety by treating the bromo compound of formula IIa with cuprous cyanide in an inert solvent such as 1-methyl-2-pyrrolidinone or the like, at or near the reflux temperature of the reaction mixture. Thereafter, the reaction mixture is treated with a solution of water, hydrochloric acid and ferric chloride. The desired nitrile of formula IIb is recovered according to known procedures, such as crystallization or the like.

An acid of formula VIII, as well as compounds of formulas I and II, wherein A is hydroxy, can be converted to the corresponding ester by known procedures. For instance, an alkali metal salt of an acid as described above, such as the sodium salt, can be reacted with a substituted or unsubstituted alkyl halide utilizing known reaction conditions, for example, in an inert solvent such as dimethylformamide, or the like, at a temperature in the range of from about room temperature to the reflux temperature of the reaction mixture.

A nitrile of formula IIb can be converted to an acid of formula VII by hydrolysis with a mineral acid, such as, sulfuric acid, hydrochloric acid or the like, in the presence of a solvent, such as, acetic acid, propionic acid, or the like.

An acid of formula VIII, as well as compounds of formulas I and II wherein A is hydroxy, can be converted to the corresponding amide by known procedures. For example, an acid as described above, is treated with thionyl chloride whereby the corresponding acid chloride is obtained. The latter is then treated with the corresponding amine, for example, treated with ammonia, dimethylamine, 3-diethylaminopropylamine, or the like, in the presence of a solvent such as tetrahydrofuran. The desired amine is then recovered according to known procedures such as crystallization.

An acid of formula VIII, as well as compounds of formulas I and II, wherein A is hydroxy, can be converted to the corresponding di-($C_1$-$C_7$)amino-($C_2$-$C_7$)alkyl ester by known procedures. For example, an acid as described above, is treated with the corresponding di-($C_1$-$C_7$)alkylamino-($C_2$-$C_3$)alkyl halide under reflux conditions in a solvent, for example, an alkanol such as isopropanol or the like, and the product is recovered according to known procedures, such as crystallization; or said compound is treated with thionyl chloride whereby the corresponding acid chloride is obtained, the latter compound is reacted with a di-($C_1$-$C_7$)alkylamino-($C_2$-$C_7$)alkanol in an inert solvent, such as tetrahydrofuran or the like, at a temperature in the range of from about 0° C. to about 100° C., and thereafter the desired end product is recovered by known procedures, such as crystallization or the like.

A compound of formula II, wherein $R_{10}$ is 5-tetrazolyl can be prepared from the corresponding compound of formula IIb. More specifically, the corresponding compound of formula IIb is treated with an alkali metal azide, such as potassium azide, sodium azide, or the like, in the presence of ammonium chloride. The reaction is suitably carried out in the presence of a solvent such as a polar aprotic solvent, for example, dimethylsulfoxide, dimethylformamide, or the like. The desired tetrazolyl compound is then recovered according to known procedures, for example, crystallization, or the like.

A compound of formula II wherein A is pivaloyloxymethoxy can be prepared by treating the corresponding compound of formula VIII with a tri-lower alkylamine and chloromethyl pivalate in an inert solvent such as dimethylformamide or the like, at a temperature in the range of from room temperature to about 120° C. The desired end product can be recovered according to known procedures, such as crystallization.

SCHEME III

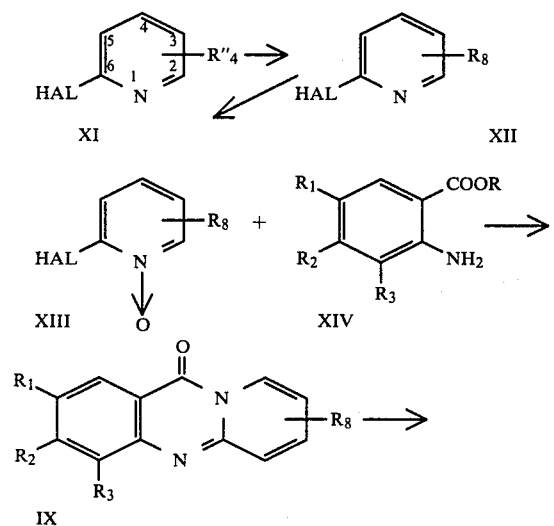

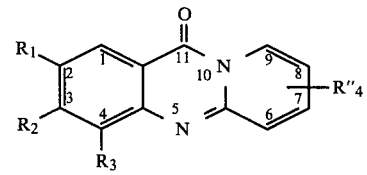

wherein R is as previously described; $R_4''$ is hydroxy-lower alkyl; $R_8$ is acyloxy-lower alkyl; and $R_1$, $R_2$, and $R_3$, independently, are hydrogen, lower alkyl, lower alkoxy, lower alkylthio, halogen, cyclopropyl, cyclobutyl, or hydroxy; provided that at least one of $R_1$, $R_2$ and $R_3$ is other than hydrogen, that in formula XI $R_4''$ is a substituent only in position 3, 4 or 5, that in formulas XII and XIII $R_8$ is a substituent only in position 3, 4 or 5, and that in formulas IX and X, $R_8$ and $R_4''$, respectively, are substituents only in position 6, 7 or 8.

In Scheme III, a halopyridine of formula XI, a known compound or a compound which can be prepared according to known procedures, is treated with an acylhalide such as benzoyl chloride, utilizing known reaction conditions, to yield the halopyridine of formula XII. A halopyridine of formula XII is converted to the compound of formula XIII with a peroxidizing agent such as m-chloroperbenzoic acid in the presence of an inert solvent, for example, a halogenated hydrocarbon such as methylene chloride. The resulting reaction mixture is neutralized with an alkali metal hydroxide such as sodium hydroxide, and thereafter, the resulting N-oxide of formula XIII is recovered. The N-oxide of formula XIII is then condensed with an anthranilic acid or ester of formula XIV, at a temperature in the range of from about 100° C. to about 200° C., with or without a solvent. The reaction is conducted in the presence of a catalytic amount of an alkali metal iodide, such as sodium iodide, potassium iodide, cesium iodide, or the like. Solvents which may be utilized in the reaction are high boiling solvents such as acetic acid, diglyme, triglyme, or the like. The reaction is conveniently carried out at atmospheric pressure. The reaction product, i.e., a compound of formula IX, can be recovered according to known procedures, such as crystallization, or the like. The compound of formula IX is converted to the compound of formula X by treatment with a mineral acid such as concentrated hydrochloric acid, in the presence of a solvent, for example, an alkanol such as ethanol, and the desired end product is then recovered according to known procedures, for example, by recrystallization from methanolic hydrogen chloride.

Alternatively, in Scheme III, a halopyridine of formula XII can be condensed directly with an anthranilic acid or ester of formula XIV, under conditions similar to those described above for the condensation of N-oxide of formula XIII and the compound of formula XIV, to yield a compound of formula IX.

The compounds of formulas I and II, when A is hydroxy, form salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium ethanolate, potassium ethanolate, and the like; organic bases such as piperidine, diethylamine, N-methylglucamine, and the like.

The compounds of formulas I and II also form salts with pharmaceutically acceptable acids. Exemplary of such acids are both pharmaceutically acceptable organic and inorganic acids, such as methanesulfonic acid, p-toluenesulfonic acid, hydrochloric acid, hydrobromic acid, sulfuric acid or the like.

The compounds of formula I, as well as the compounds of formula II and their pharmaceutically acceptable salts inhibit cutaneous anaphylaxis in rats, and are therefore useful in the prevention of allergic reactions, for example, they are useful in the prophylactic treatment of bronchial asthma. The anti-anaphylactic activity can be demonstrated by the passive cutaneous anaphylaxis assay (PCA test) in the rat. This test involves passive local sensitization of rats by intra-dermal injection of anti-sera. After a latent period of 24 hours, the test compound, in this case, a pyrido[2,1-b]quinazoline, is given intraperitoneally followed after 5 minutes by an intravenous injection of reagen and Evans blue dye. The events associated with localized antigen-antibody reaction lead to the formation of skin wheals whose sizes are measured. The ability of the test compound to decrease the size of the wheals compared to controls is taken as a measure of its activity.

When a compound of the invention, such as 2-methoxy-11-oxo-11H-pyrido[2,1-b]quinazoline-8-carboxylic acid is utilized as the test compound at a dose of 16 mg/kg intraperitoneally, the reduction in the wheal size is 63%. When the sodium salt of 2-methoxy-11-oxo-11H-pyrido[2,1-b]quinazoline-8-caboxylic acid is utilized as the test compound at a dose of 16 mg/kg intraperitoneally, the reduction in the wheal size is 86%.

The anti-allergic activity of the compounds of formulas I and II can also be demonstrated in the actively sensitized guinea pig (IgG). In this test, the guinea pig is sensitized intraperitoneally with horse serum on day 1 and then the animal is challenged intravenously on days 11-14 with antigen (horse serum) which immediately initiates the immediate type hypersensitive reaction (IHR bronchospasm). When an anti-allergic compound is administered intravenously prior to the antigen, the IHR is blocked, thereby preventing bronchospasm.

When 2-methoxy-11-oxo-11H-pyrido[2,1-b]quinazoline-8-carboxylic acid is utilized in the foregoing test at an oral dose of 200 mg/kg, the percent inhibition of bronchospasm is 65%. When the foregoing compound is administered intravenously at a dose of 20 mg/kg, the percent inhibition of bronchospasm is 54%.

The anti-allergic activity can also be demonstrated in the passively sensitized rat (IgE). In this test, a rat is administered anti-sera intravenously 18 hours prior to the intravenous antigen (egg albumin) challenge. The antigen challenge originates the IHR. When an anti-allergic compound is administered intravenously prior to the antigen challenge, it inhibits IHR and prevents bronchospasm.

When 2-methoxy-11-oxo-11H-pyrido[2,1-b]quinazoline-8-carboxylic acid is utilized in the foregoing test at an oral dose of 10 mg/kg, the percent inhibition of bronchospasm is 59%. When the foregoing compound is administered intravenously at a dose of 10 mg/kg., the percent inhibition of bronchospasm is 83%.

The compounds of formulas I and II and their pharmaceutically acceptable addition salts can be administered orally or parenterally as anti-allergic agents, for example in the prophylactic treatment of bronchial asthma, with dosage adjustments for individual requirements. They can be administered thereapeutically, for example, orally or parenterally, by incorporating a therapeutic dosage in a conventional dosage form, such as tablets, capsules, elixirs, suspensions, solutions or the like. They can be administered in mixture with conventional pharmaceutical carriers or excipients, such as, for example, corn starch, calcium stearate, magnesium carbonate, calcium silicate, dicalcium phosphate, talc, lactose, and the like. Moreover, they can be administered in the presence of buffers, or agents used to adjust to isotonicity, and the pharmaceutical dosage forms can, if desired, be subjected to conventional pharmaceutical expedients such as, for example, sterilization. As stated above, the dosage can be adjusted to individual requirements. They can also contain other therapeutically valuable substances.

The quantity of active medicament which is present in any of the abovedescribed dosage forms is variable. It is preferred, however, to provide capsules or tablets containing from about 10 mg. to about 20 mg. of the formula I or II base or an equivalent amount of a medicinally acceptable acid addition salt thereof.

The frequency with which any such dosage form will be administered to a patient will vary, depending upon the quantity of active medicament present therein and the needs and requirements of the patient. Under ordinary circumstances, however, up to about 20 mg/kg. of the compound can be administered daily in several dosages. It is to be understood, however, that the dosages set forth therein are exemplary only and that they do not, to any extent, limit the scope or practice of this invention.

The following Examples further illustrate the invention. All temperatures are in degrees Centigrade.

EXAMPLE 1

Preparation of
2-bromo-11-oxo-11H-pyrido[2,1-b]quinazoline hydrochloride

An intimate mixture of 100.0 g. of 2-chloropyridine, 83.0 g. of 5-bromoanthranilic acid, and 1.0 g. potassium iodide was heated to a bath temperature of 145°-150° overnight under a stream of argon. On cooling, the crude product was triturated with 150 ml. of boiling ethanol and was collected to give 105.4 g. (86%) of 2-bromo-11-oxo-11H-pyrido[2,1-b]quinazoline hydrochloride, mp 280°-282° dec. The analytical sample was obtained from aqueous hydrochloric acid dimethylforamide-ethanol and melted at 278°-281°.

EXAMPLE 2

Preparation of
11-oxo-11H-pyrido[2,1-b]quinazoline-2-carboxylic acid

A suspension of 15.00 g. of 2-bromo-11-oxo-11H-pyrido[2,1-b]quinazoline hydrochloride and 3.60 g. of calcium hydroxide in 105 ml. of 5% aqueous dimethylformamide was placed in a 6 oz. Fischer-Porter bottle and the atmosphere was replaced with carbon monoxide. Approximately 10 ml. of nickel carbonyl was introduced through a syringe needle and the carbon monoxide pressure was raised to 20 lbs. As the bath temperature was raised to 110°-115°, the pressure rose to ~40 pounds and the yellow suspension became a green solution. After a total of 25 hours, the mixture was allowed to cool, was diluted with 300 ml. of 1 N hydrochloric acid and was filtered. The filter cake was triturated with hot ethanol-dimethylformamide and the filtrate deposited 3.23 g. of crude 11-oxo-11H-pyrido[2,1-b]quinazoline-2-carboxylic acid, mp>310°. The filter cake was dissolved in 200 ml. of dimethylformamide containing 10 ml. of ammonia, the solution was filtered, and the filtrate was diluted with water and acetic acid to precipitate an additional 3.37 g. of 11-oxo-11H-pyrido[2,1-b]quinazoline-2-carboxylic acid, mp>310°. The two crops were combined and triturated with ethanol-dimethylformamide-acetic acid to give 6.35 g. (48%) of 11-oxo-11H-pyrido[2,1-b]quinazoline-2-carboxylic acid, mp 354°.

EXAMPLE 3

Preparation of 8-methyl-11-oxo-11H-pyrido[2,1-b]quinazoline-2-carboxylic acid An intimate mixture of 5.0 g. of 5-bromoanthranilic acid, 6.7 g. of 2-chloro-5-methylpyridine, and 67 mg. of potassium iodide was heated to a bath temperature of 145° for 8 hours. On cooling, the mixture was diluted with 15 ml. of ethanol and filtered to give 3.57 g. (48%) of 2-bromo-8-methyl-11-oxo-11H-pyrido[2,1-b]quinazoline, mp 277°–281°.

A mixture of 3.00 g. of the above pyridoquinazoline and 0.73 g. of calcium hydroxide in 21 ml. of 5% aqueous dimethylformamide was placed in a 3 ounce Fischer-Porter bottle under a carbon monoxide atmosphere. Approximately 3 ml. of nickel carbonyl was added and the bottle was pressurized to 20 pounds with carbon monoxide. The bath temperature was raised to 115° for 24 hours and on cooling, the mixture was diluted with 15 ml. of 6 N hydrochloric acid. After stirring overnight, the suspension was filtered and the solid collected was recrystallized from dimethylformamide and from dimethylformamide-ether to give 1.54 g. (67%) of 8-methyl-11-oxo-11-H-pyrido[2,1-b]quinazoline-2-carboxylic acid, mp 359°.

EXAMPLE 4

Preparation of 6-chloro-3-(N-diethylaminoethylcarbamoyl)pyridine hydrochloride A solution of 5.0 g. of 6-chloroicotinic acid and 8.56 ml. of diphenylphosphorylazide in 25 ml. of dimethylformamide was cooled in an ice bath as 4.27 ml. of N,N-diethylethylenediamine was added dropwise. On completion of the addition, the reaction mixture was allowed to stand at room temperature overnight and was poured into 500 ml. of water. The aqueous solution was extracted 3×500 ml. dichloromethane and the combined organic layers were washed with water, dried over potassium carbonate and evaporated to an oil which was dissolved in 15 ml. of ethanol and carefully acidified with hydrochloric acid in tetrahydrofuran. On cooling, 5.62 g. (61%) of 6-chloro-3-(N-diethylaminoethylcarbamoyl)-pyridine hydrochloride, mp 182°–184° was obtained. The filtrate yielded an additional 1.74 g. (19%) of 6-chloro-3-(N-diethylaminoethylcarbamoyl)-pyridine hydrochloride, mp 171°–181°.

EXAMPLE 5

Preparation of N-(2-diethylaminoethyl)-2-methoxy-11-oxo-11H-pyrido[2,1-b]quinazoline-8-carboxamide hydrochloride A suspension of 4.4 g. of 6-chloro-3-(N-diethylaminoethylcarbamoyl)pyridine hydrochloride, 3.28 g. of 5-methoxyanthranilic acid methyl ester hydrochloride and 0.2 g. of potassium iodide in 4 ml. of triglyme was heated to a bath temperature of 150° under a stream of argon for 5 hours. On cooling, the reaction mixture was triturated with ether and filtered to give a yellow solid which was recrystallized from ethanolether to give 3.47 g. (57%) of N-(2-diethylaminoethyl)-2-methoxy-11-oxo-11H-pyrido-[2,1-b]quinazoline-8-carboxamide hydrochloride, mp 249°–251°.

EXAMPLE 6

Preparation of 2-methoxy-11-oxo-11H-pyrido[2,1-b]quinazoline-8-carboxamide

A suspension of 10.24 g. of 2-chloro-5-carbamoylpyridine, 14.26 g. of 5-methoxyanthranilic acid and 300 mg. of potassium iodide in 30 ml. of triglyme was heated to a bath temperature of 155° overnight. On cooling, the mixture was diluted with 30 ml. of ethanol and the precipitate was collected to give 15.21 g. (76%) of 2-methoxy-11-oxo-11H-pyrido[2,1-b]quinazoline-8-carboxamide, mp>310°. Recrystallization from dimethylformamide-acetic acid and from acetic acid gave the analytical sample, mp 326°.

EXAMPLE 7

Preparation of 8-cyano-2-methoxy-11-oxo-11H-pyrido[2,1-b]quinazoline

A mixture of 8.3 g. of 2-chloro-5-cyanopyridine, 13.04 g. of 5-methoxyanthranilic acid and 0.2 g. of potassium iodide in 10 ml. of triglyme was heated to a bath temperature of 170° for 4 hours under a slow stream of argon. On cooling, the mixture was triturated with methanol and ether and filtered. The solid thus obtained was recrystallized from methanol to give 6.02 g. (40%) of 8-cyano-2-methoxy-11-oxo-11H-pyrido[2,1-b]quinazoline, mp 282°–284°. A further crystallization from methanolmethylene chloride gave the analytical sample, mp 284°–285°.

EXAMPLE 8

Preparation of 2-methoxy-11-oxo-11H-8-(1H-tetrazol-5-yl)pyrido[2,1-b]quinazoline hemihydrochloride A suspension of 7.0 g. of 8-cyano-2-methoxy-11-oxo-11H-pyrido[2,1-b]quinazoline, 2.24 g. of sodium azide and 1.89 g. of ammonium chloride in 70 ml. of dimethylformamide was heated to a bath temperature of 100° overnight and an additional 2.24 g. of sodium azide and 1.89 g. of ammonium chloride were added. After an additional 6 hours, the reaction mixture was allowed to cool and was filtered. The yellow solid collected was recrystallized from aqueous methanol containing hydrochloric acid to give 5.55 g. (68%) of 2-methoxy-11-oxo-11H-8-(1H-tetrazol-5-yl)pyrido[2,1-b]quinazoline, mp 286° dec. The filtrate deposited a second crop of 2.28 g. (29%), mp 285° dec.

EXAMPLE 9

Preparation of methyl-2-methoxy-11-oxo-11H-pyrido[2,1-b]quinazoline-8-carboxylate hydrochloride A. A suspension of 6.10 g. of 2-methoxy-11-oxo-11H-pyrido[2,1-b]quinazoline-8-carboxylic acid and 2.52 g. of sodium bicarbonate in 20 ml. of hexamethyl phosphoramide and 3.0 ml. of methyl iodide was stirred at room temperature for 72 hours, and an additional 2.52 g.

of sodium bicarbonate and 3.0 ml. of methyl iodide were added. After an additional 48 hours, the reaction mixture was diluted with water and the precipitate was collected. Trituration of the filter cake with boiling methanol gave 0.69 g. (11%) of methyl 2-methoxy-11-oxo-11H-pyrido[2,1-b]quinazoline-8-carboxylate mp 205°-208° and a second crop amounted to 0.43 g. (7%), mp 195°-200°. A portion of this material was crystallized from methanol-ether-hydrochloric acid to give the hydrochloride salt, mp 235°-238°.

B. A suspension of 2.40 g. of 2-methoxy-11-oxo-11H-pyrido[2,1-b]quinazoline-8-carboxylic acid and 2.4 g. of potassium carbonate in 25 ml. of dimethylformamide and 2.5 ml. of methyl iodide was stirred at room temperature for 48 hours. The resulting mixture was diluted with 75 ml. of water and the yellow precipitate was collected, 2.36 g. (94%), mp 188°-195°. Recrystallization from methanol-hydrochloric acid-acetic acid gave 2.24 g. (79%) of methyl 2-methoxy-11-oxo-11H-pyrido[2,1]quinazoline-8-carboxylate hydrochloride, mp 228°-231°.

EXAMPLE 10

Preparation of 2-methoxy-11-oxo-11H-pyrido[2,1-b]quinazoline-8-carboxylic acid (2-diethylaminoethyl) ester hydrochloride A 12.5 g. portion of diethylaminoethyl chloride hydrochloride was partitioned between 50 ml. of 1 N sodium hydroxide and 60 ml. of ether. The combined ether layers were washed with water and brine, were dried over potassium carbonate and were evaporated in the cold. The resulting oil was added to a mechanically stirred suspension of 5.00 g. of 2-methoxy-11-oxo-11H-pyrido[2,1-b]quinazoline-8-carboxylic acid in 60 ml. of dry isopropanol and the mixture was heated to reflux for 2 hours. On cooling, the solids were collected and recrystallized from methanol-ether to give 5.72 g. (76%) of 2-methoxy-11-oxo-11H-pyrido[2,1-b]quinazoline-8-carboxylic acid (2-diethylaminoethyl) ester hydrochloride, mp 250°-253°. A further crystallization from dimethylformamideacetic acid raised the melting point to 255°-258°.

EXAMPLE 11

Preparation of 8-(N,N-dimethylcarbamoyl)-2-methoxy-11-oxo-11H-pyrido[2,1-b]quinazoline A solution of 6.0 g. of 2-methoxy-11-oxo-11H-pyrido[2,1-b]quinazoline-8-carboxylic acid in 100 ml. of thionyl chloride was refluxed for 3 hours. The reaction was evaporated to dryness and the solid residue was suspended in 200 ml. of dry tetrahydrofuran. Dimethylamine was bubbled through the mixture until the color had changed from yellow to green-yellow and the solids were collected. The solids were dissolved in methanol, the solution was filtered and evaporated to dryness. The residue was recrystallized from 500 ml. of ethyl acetate to give 4.0 g. (61%) of 8-(N,N-dimethylcarbamoyl)-2-methoxy-11-oxo-11H-pyrido[2,1-b]quinazoline, mp 190°-196°. Recrystallization from ethyl acetate-hexane and then from ethyl acetate raised the melting point to 197°-199°.

EXAMPLE 12

Preparation of 6-chloro-3-pyridinemethanolbenzoate

To an ice cooled solution of 24.41 g. of 2-chloro-5-hydroxymetyl-pyridine in 250 ml. of dry methylene chloride and 27.0 ml. of dry triethylamine was added 23.0 ml. of benzoyl chloride dropwise. The resulting mixture was stirred at 0° for 1 hour and at room temperature for 2 hours. It was next diluted with 500 ml. of methylene chloride and washed with 100 ml. portions of water, saturated sodium bicarbonate and saturated sodium chloride. Drying (potassium carbonate) and evaporation gave 45.4 g. of a yellow semi-solid which was distilled through a short path apparatus to give 41.51 g. (98%) of crude 6-chloro-3-pyridinemethanolbenzoate, boiling point 150°-160°/0.1-0.2 mm.

Recrystallization from ether-ligroin gave, after filtration to remove some insoluble material, 33.42 g. (79%), melting point 58°-60°. The analytical sample was obtained from ether-hexane and melted at 59°-62°.

EXAMPLE 13

Preparation of 6-chloro-3-pyridine methanolbenzoate, N-oxide

A solution of 33.42 g. of 6-chloro-3-pyridinemethanolbenzoate and 75 g. of m-chloroperbenzoic acid in 1800 ml. of methylene chloride was stirred at room temperature for 5 days and was washed 2×500 ml. 1 N sodium hydroxide, 2×500 ml. water, 1×500 ml. brine and was dried (potassium carbonate). Evaporation gave a yellow solid which on crystallization from ethyl acetate-hexane gave 25.87 g. (73%) of 6-chloro-3-pyridine methanolbenzoate, N-oxide, mp 116°-121°. The analytical sample was obtained from ethyl acetate, mp 120°-123°.

EXAMPLE 14

Preparation of 8-hydroxymethyl-2-methoxy-11H-pyrido[2,1-b]quinazoline-11-one benzoate A suspension of 5.00 g. of 5-methoxyanthranilic acid and 3.90 g. of 6-chloro-3-pyridine methanolbenzoate, N-oxide in 9 ml. of triglyme was heated to a bath temperature of 120° overnight. On cooling, the reaction mixture was triturated with 15 ml. of ethanol and was filtered to give 3.79 g. (71%) of crude 8-hydroxymethyl-2-methoxy-11H-pyrido[2,1-b]quinazoline-11-one benzoate, mp 206°-219°. Trituration with boiling methanol gave 1.75 g. (33%), mp 226°-229°. Two recrystallizations from aqueous acetic acid gave a sample, mp 228°-230°.

EXAMPLE 15

Preparation of 8-hydroxymethyl-2-methoxy-11H-pyrido[2,1-b]quinazoline-11-one hydrochloride A solution of 1.75 g. of 8-hydroxymethyl-2-methoxy-11H-pyrido[2,1-b]quinazoline-11-one benzoate in 10 ml. of concentrated hydrochloric acid and 7 ml. of ethanol was refluxed overnight. On cooling 0.60 g. (42%) of 8-hydroxymethyl-2-methoxy-11H-pyrido-[2,1-b]quinazoline-11-one hydrochloride, mp 248°-251° dec., separated and the filtrate afforded an additional 0.72 g. (51%), mp 244°-248°. The analytical sample was obtained from methanolic hydrochloric acid-ether and melted, 253°-255° dec.

EXAMPLE 16

Preparation of 2-nitro-5-methylthiobenzoic acid

To a solution of 50 ml. of methyl mercaptan in 200 ml. of dimethylformamide was added 48 g. of sodium hydride portionwise at −40°. On completion of the ensuing reaction, 100.0 g. of 5-chloro-2-nitrobenzoic acid was added. The reaction temperature was allowed to come up to −10°, was lowered back to −40°, and the excess reagent was quenched with 1 N hydrochloric acid. After 2 hours stirring at room temperature, the product was collected, 102.3 g. (97%), mp 165°–169°. Recrystallization from methanolethyl acetate gave 52.14 g., mp. 173°–174°. The analytical sample was obtained from ethyl acetate, mp 174°–175°.

EXAMPLE 17

Preparation of methyl 2-amino-5-methylthiobenzoate

To an ice cold solution of 52.1 g. of 2-nitro-5-methylthiobenzoic acid in 250 ml. of methanol was added an ethereal solution of diazomethane until thin layer chromatography indicated the reaction was complete. The resulting solution was evaporated to dryness and used as such. In one case the crude product was crystallized from methanol to give yellow needles of methyl 2-nitro-5-methylthiobenzoate, mp 53°–54°.

The crude product from above, 55.5 g., was suspended together with 55.5 g. of iron powder in 280 ml. of glacial acetic acid. The bath temperature was raised to 125° over 30 minutes and the resulting grey suspension was permitted to cool and was filtered through celite. Evaporation gave a dark, oily residue which was triturated with methanolic hydrochloric acid to give a white solid which was crystallized from methanol-ether to give 33.32 g. (58%) of methyl 2-amino-5-methylthiobenzoate hydrochloride, mp 193°–194°. A second crop of 7.35 g. (13%), m.p. 191°–192° was obtained from the filtrate. The analytical sample was obtained from methanol-ether, mp 196°–197°.

EXAMPLE 18

Procedure A-Preparation of 2-substituted-pyrido[2,1-b]quinazoline-8-carboxylic acid The synthesis of 2-substituted-pyrido[2,1-b]quinazoline-8-carboxylic acids via condensation of the appropriate anthranilic acid with 6-chloronicotinic acid is illustrated by the synthesis of 2-methyl-11-oxo-11H-pyrido[2,1-b]quinazoline-8-carboxylic acid. A suspension of 28.7 g. of 5-methylanthranilic acid, 25.0 g. of 6-chloronicotinic acid and 1.32 g. of potassium iodide in 50 ml. of triglyme was heated to a bath temperature of 150° overnight under a stream of argon. On cooling, the mixture was triturated with ethanol and filtered to give 31.8 g. of a yellow solid, mp 295°–310°. Recrystallization from dimethylformamide-acetic acid gave 15.3 g. (38%) of 2-methyl-11-oxo-11H-pyrido[2,1-b]quinazoline-8-carboxylic acid, mp >310°.

Procedure B-Preparation of 2-ethoxy-11-oxo-11H-pyrido[2,1-b]quinazoline-8-carboxylic acid The reaction of an anthranilic acid hydrochloride with 6-chloronicotinic acid is illustrated by the preparation of 2-ethoxy-11-oxo-11H-pyrido[2,1-b]quinazoline-8-carboxylic acid. A suspension of 7.5 g. of 5-ethoxyanthranilic acid hydrochloride, 6.3 g. of 6-chloronicotinic acid and 1.2 g. of potassium iodide in 12 ml. of triglyme was heated to a bath temperature of 145°–150° overnight. On cooling, the mixture was triturated with ethanol and filtered to give 7.7 g., mp 260°–265°. Recrystallization from dimethylformamide gave 4.14 g. (42%) of 2-ethoxy-11-oxo-11H-pyrido[2,1-b]quinazoline-8-carboxylic acid, mp 285°–287°.

Procedure C-Preparation of 2-methoxy-11-oxo-11H-pyrido[2,1-b]quinazoline-8-carboxylic acid The reaction of substituted methyl anthranilatehydrochlorides with 6-chloronicotinic acid is illustrated by the synthesis of 2-methoxy-11-oxo-11H-pyrido[2,1-b]quinazoline-8-carboxylic acid. A suspension of 134 g. of methyl 5-methoxyanthranilate hydrochloride, 106.7 g. of 6-chloronicotinic acid, and 9.0 g. of potassium iodide in 300 ml. of triglyme was heated to a bath temperature of 150° overnight. The resulting suspension was diluted with 200 ml. of ethanol and was filtered to give 177.9 g., mp 278°–290°. Recrystallization from 2.5 l. of dimethylformamide and 500 ml. of glacial acetic acid gave 93.3 g. (56%) of 2-methoxy-11-oxo-11H-pyrido[2,1-b]quinazoline-8-carboxylic acid, mp 22 310°.

| Compound | Starting Material | Method of Preparation Procedure | % Yield | mp °C | Recrystallization Solvent[a] |
|---|---|---|---|---|---|
| 2-Methoxy-11-oxo-11H-pyrido-[2,1-b]quinazoline-8-carboxylic acid | 5-Methoxyanthranilic acid | A | 46 | 318[b] | DMF-HOAc |
| 2-Methoxy-11-oxo-11H-pyrido-[2,1-b]quinazoline-8-carboxylic acid | Methyl-5-methoxyanthranilate hydrochloride | C | 56 | 310 | DMF-HOAc |
| 2-Ethoxy-11-oxo-11H-pyrido-[2,1-b]quinazoline-8-carboxylic acid | 5-Ethoxyanthranilic acid | B | 42 | 295–300 | DMF |
| 11-Oxo-2-propoxypyrido-11H-[2,1-b]-quinazoline-8-carboxylic acid | 5-Propoxyanthranilic acid hydrochloride | B | 30 | 275–277 | DMF |
| 2-Isopropoxy-11-oxo-11H-pyrido-[2,1-b]quinazoline-8-carboxylic acid | 5-Isopropoxyanthranilic acid hydrochloride | B | 32 | 278–279 | Pr-DMEA[c] |
| 2-Butoxy-11-oxo-11H-pyrido[2,1-b]-quinazoline-8-carboxylic acid | 5-Butoxyanthranilic acid hydrochloride | B | 33 | 254–256 | DMF |
| 2-Amyloxy-11-oxo-11H-pyrido-[2,1-b]quinazoline-8-carboxylic acid | 5-Amyloxyanthranilic acid hydrochloride | B | 22 | 237–240 | DMF |
| 2-Methyl-11-oxo-11H-pyrido-[2,1-b]quinazoline-8-carboxylic acid | 5-Methylanthranilic acid | A | 38 | 320[b] | DMF-HOAc |
| 2-Chloro-11-oxo-11H-pyrido-[2,1-b]quinazoline-8-carboxylic acid | 5-Chloroanthranilic acid | A | 33 | 328[b] | DMF-HOAc |

-continued

| Compound | Starting Material | Method of Preparation Procedure | % Yield | mp °C. | Recrystallization Solvent[a] |
|---|---|---|---|---|---|
| 2-Methylthio-11-oxo-11H-pyrido-[2,1-b]quinazoline-8-carboxylic acid | 5-Methylthioanthranilic acid methyl ester hydrochloride | C | 48 | 337[b] | Pr-DMEA[c] |
| 2-Hydroxy-11-oxo-11H-pyrido-[2,1-b]quinazoline-8-carboxylic acid | 5-Hydroxyanthranilic acid | A | 43 | 349[b] | DMF-HOAc |
| 2,3-Dimethoxy-11-oxo-11H-pyrido-[2,1-b]quinazoline-8-carboxylic acid | 4,5-Dimethoxyanthranilic acid methyl ester hydrochloride | C | 43 | 316–317 | DMF-HOAc |
| 2,4-Dimethoxy-11-oxo-11H-pyrido-[2,1-b]quinazoline-8-carboxylic acid | 3,5-Dimethoxyanthranilic acid methyl ester | C | 13 | 353[b] | Pr-DMEA[c] |
| 2-Isopropyl-11-oxo-11H-pyrido[2,1-b]quinazoline-8-carboxylic acid | 5-Isopropylanthranilic acid | B | 11.8 | 318–320 | DMF |
| 11-Oxo-11H-2,3,4-trimethoxypyrido-[2,1-b]quinazoline-8-carboxylic acid ¼ hydrate | 3,4,5-Trimethoxyanthranilic acid methyl ester | C | 9 | 288–289° | Pr-DMEA[c] |
| 3-Methoxy-11-oxo-11H-pyrido-[2,1-b]quinazoline-8-carboxylic acid | 4-Methoxyanthranilic acid methyl ester | C | 51 | 304–306° | Pr-DMEA[c] |
| 3-Chloro-11-oxo-11H-pyrido[2,1-b]-quinazoline-8-carboxylic acid ¼ hydrate | 4-Chloroanthranilic acid | A | 22 | 307–314° | DMF-HOAc |
| 4-Methoxy-11-oxo-11H-pyrido-[2,1-b]quinazoline-8-carboxylic acid ¼ hydrate | 3-Methoxyanthranilic acid hydrochloride | B | 7 | 304–306° | PrDMEA[c] |
| 4-Chloro-11-oxo-11H-pyrido-[2,1-b]quinazoline-8-carboxylic acid | 3-Chloroanthranilic acid | A | 34 | 367[,b] | DMF-HOAc |

[a]DMF = dimethylformamide; HOAc = acetic acid; Pr = isopropyl alcohol; DMEA = N,N-dimethylethanol amine
[b]Melting point was determined on a Dupont Instruments Model 900 thermal analyzer
[c]Compounds recrystallized from this solvent system were obtained as the free acids by precipitation from water with acetic acid

EXAMPLE 19

Preparation of crude 2-methoxy-11-oxo-11H-pyrido[2,1-b]quinazoline-8-carboxylic acid hydrochloride A 1.0 l. three-neck flask was equipped with a mechanical stirrer, argon inlet, short path condenser and receiver, oil bath, hot plate, thermowatch, temperature controller and bath thermometer. The flask was flushed with argon and charged with 135 g. of 5-methoxyanthranilic acid, 135 g. of 6-chloronicotinic acid, 2.0 g. of potassium iodide and 400 ml. of triethylene glycol dimethyl ether (triglyme). This reaction mixture was stirred and heated under a slow stream of argon. When the bath temperature reached about 140° C. most of the solid had dissolved. Upon continued heating the product slowly precipitated as a yellow solid. The bath temperature was maintained at 150° C. overnight and a slow stream of argon was maintained over the stirred reaction mixture. The thick mixture which resulted was cooled to less than 50° C. and was then triturated with 200 ml. of ethanol. The resulting slurry was vacuum filtered, washed with 100 ml. of absolute ethanol, pressed dry and then dried overnight at 60° C. under high vacuum to yield 326 g. of crude product. This material is 2-methoxy-11-oxo-11H-pyrido[2,1-b]quinazoline-8-carboxylic acid hydrochloride.

EXAMPLE 20

Purification of 2-methoxy-11-oxo-11H-pyrido[2,1-b]quinazoline-8-carboxylic acid hydrochloride via the ethylenediamine salt 326 g. of the above crude hydrochloride was dissolved in 6.2 l. of pyridine (25 ml/g assuming 100% theoretical yield) and heated to reflux in a 12 l. three-neck flask. To the stirred and refluxing solution was added 81.1 ml. of distilled ethylenediamine over a period of 5 minutes and the resulting slurry was refluxed for 10 minutes. The heating mantle was then removed and the stirred reaction was allowed to cool (about 4 hours) to room temperature. The crystals were collected by vacuum filtration, washed with 3×250 ml. of pyridine, pressed dry and dried to constant weight in vacuo at 60° overnight to yield 189.8 g. of the ethylenediamine salt of the product as a yellow solid. This material was recrystallized by dissolving in 500 ml. of hot water. The hot aqueous solution was added to a 12 l. three-neck flask containing 500 ml. of refluxing pyridine and then 5.2 l. of pyridine was added slowly to the refluxing solution. Upon completion of the addition, an atmospheric distillation of the pyridine-water azeotrope was begun. During the distillation an additional 1.0 l. of pyridine was added slowly (over a 1 hour period) to the stirred mixture and product began to separate. Distillation was continued until the head temperature had reached 110° C. and was then stopped (approximately 2.7 l. of distillate was collected) and the mixture was allowed to cool below reflux temperature. 27 ml. of distilled ethylenediamine was then added and the stirred mixture was allowed to cool to room temperature for 3 hours. The resulting crystals were collected, washed with a small portion of pyridine and pressed dry rapidly. The product (about 200 g.) was used directly or stored in vacuo.

EXAMPLE 21

Regeneration of Purified 2-methoxy-11-oxo-11H-pyrido[2,1-b]quinazoline-8-carboxylic acid 200 g. of the entire recrystallized ethylenediamine salt of the captioned quinazoline was dissolved in 1.0 l. of water and stirred at room temperature while a solution of 300 ml. of glacial acetic acid dissolved in 1.5 l. of water was added dropwise over a period of 2 hours. The final pH of the mixture was about 4 by Accutint paper, range no. 70. The resulting crystals were collected, washed with 2×1.0 l. of water and dried overnight at 100° C. in vacuo to yield 95 g. of yellow solid melting at 322° C. This material was crystallized by dissolving in 1.25 l. refluxing pyridine. The hot solution was quickly vacuum filtered through a steam jacketed Buchner funnel. The filter and flask were washed with 300 ml. of boiling pyridine. The filtrate was transferred to a 2 l. wide mouth erlenmeyer flask and heated to redissolve all the solids. The resulting solution was allowed to cool slowly to room temperature and the slurry was then thoroughly chilled to 0° C. for 2 hours. The crystals were filtered, washed with 200 ml. of cold pyridine, pressed dry and dried in vacuo at 115° overnight under a slow stream of nitrogen to yield 87.6 g. of product (mp 325° C.).

EXAMPLE 22

Preparation of 2-methoxy-11-oxo-11H-pyrido[2,1-b]quinazoline-8-carboxylic acid sodium salt, monohydrate 27.023 G. of 2-methoxy-11-oxo-11H-pyrido[2,1-b]quinazoline-8-carboxylic acid was stirred in 50 ml. of water at room temperature as 100 ml. of 1.0 N sodium hydroxide solution was added. The resulting mixture was stirred for approximately 30 minutes until most of the solids had dissolved. The solution was then vacuum filtered to remove insolubles and the filtrate was poured into a 5 l. three-neck flask along with 1.0 l. of pyridine. The resulting slurry was heated to reflux at which temperature all of the solids dissolved. Atmospheric distillation of solvent was begun as an additional 1.0 l. of pyridine was slowly added. The quinazoline product began to separate but distillation was continued until a head temperature of 100° C. was achieved (approximately 1 l. of distillate). The slurry was then cooled to room temperature for 3 hours, filtered, washed with 2×100 ml. of pyridine and dried in vacuo at 95° overnight under a slight stream of nitrogen. This gave 30.2 g. (97.0%) of the monohydrated sodium salt captioned above as a light yellow solid.

EXAMPLE 23

Preparation of 2-methoxy-11-oxo-11H-pyrido[2,1-b]quinazoline-7-carboxylic acid

A suspension of 2.80 g. of 5-methoxyanthranilic acid, 2.65 g. of 2-chloroisonicotinic acid and 0.135 g. of potassium iodide in 13 ml. of triglyme was stirred and heated at a bath temperature of 150° for 21 hours under a stream of argon. After cooling, 40 ml. of methanol was added, and the yellow solid was removed by filtration. The crude product was purified by recrystallization of the ethylenediamine salt from pyridine, conversion back to the free acid by treatment with acetic acid and recrystallization from acetic acid to give 0.42 g. (9%) of pure 2-methoxy-11-oxo-11H-pyrido[2,1-b]quinazoline-7-carboxylic acid, mp 323°–327°.

EXAMPLE 24

Preparation of 2-methoxy-11-oxo-11H-pyrido[2,1-b]quinazoline-6-carboxylic acid

A suspension of 1.05 g. of 5-methoxyanthranilic acid, 0.99 g. of 2-chloronicotinic acid and 0.050 g. of potassium iodide in 5 ml. of triglyme was stirred and heated at a bath temperature of 150° for 17 hours under a stream of argon. After cooling, 15 ml. of methanol was added and the yellow solid was removed by filtration. The crude material was purified by recrystallization from N,N-dimethylformamide/acetic acid to give 0.67 g. (40%) of pure 2-methoxy-11-oxo-11H-pyrido[2,1-b]quinazoline-6-carboxylic acid, mp 272°–273.5°.

EXAMPLE 25

Preparation of pivaloyloxymethyl-2-methoxy-11-oxo-11H-pyrido[2,1-b]quinazoline-8-carboxylate To 0.40 g. of 2-methoxy-11-oxo-11H-pyrido[2,1-b]quinazoline-8-carboxylic acid suspended in 30 ml. of dimethylformamide was added 0.4 ml. of triethylamine. To the clear solution was added 0.4 ml. of chloromethylpivalate and the mixture was stirred and heated at a bath temperature of 100° for 19 hours. An additional 0.3 ml. of chloromethylpivalate was added and heating was continued at 100° for 4.5 hours. The solvent was removed on the oil pump, water was added, and the crude product was removed by filtration. Purification was accomplished by chromatography on 15 g. of silica gel and elution with 60% ethyl acetate-benzene. Recrystallization from methanol-water gave 0.37 g. (65%) of pure pivaloyloxymethyl-2-methoxy-11-oxo-11H-pyrido[2,1-b]quinazoline-8-carboxylate, mp 129°–131°.

EXAMPLE 26

Preparation of 2-methoxy-8-acetyl-11-oxo-11H-pyrido[2,1-b]quinazoline

A suspension of 0.526 g. of 5-methoxyanthranilic acid, 0.490 g. of 2-chloro-5-acetylpyridine and 0.030 g. of potassium iodide in 2.5 ml. of triglyme was stirred and heated at a bath temperature of 150° for 21 hours under a stream of argon. After cooling, 8 ml. of methanol was added and the brown solid was removed by filtration. Purification was accomplished by chromatography on silica gel and elution with 40% ethyl-acetate-benzene. The combined pure fractions were recrystallized from methylene chloride-ether to give 0.13 g. (14%) of pure 2-methoxy-8-acetyl-11-oxo-11H-pyrido[2,1-b]quinazoline, mp 194°–196°.

EXAMPLE 27

Preparation of 2-methoxy-11-oxo-11H-pyrido[2,1-b]quinazoline-8-acetic acid

A mixture of 0.836 g. of 5-methoxyanthranilic acid, 0.858 g. of 2-chloropyridine-5-acetic acid and 15 mg. of potassium iodide was stirred and heated at a bath temperature of 150° under argon for 1¼ hours. After cooling, the solid mass was triturated with isopropyl alcohol, and the yellow solid was filtered. The crude product was purified by recrystallization of the ethylenediamine salt from pyridine, conversion back to the free acid by treatment with acetic acid to give 0.054 g. (3.8%) of pure 2-methoxy-11oxo-11H-pyrido[2,1-b]quinazoline-8-acetic acid, mp 281°–282°.

EXAMPLE 28

Procedure J-Preparation of 2-n-butyl-11-oxo-11H-pyrido[2,1-b]quinazoline-8-carboxylic acid A suspension of 11.6 g. of 5-n-butylanthranilic acid, 9.4 g. of 6-chloronicotinic acid and 0.1 g. of potassium iodide in 20 ml. of triglyme was heated to a bath temperature of 150° C. overnight under a stream of argon. On cooling, the mixture was triturated with ethanol and water and filtered to give 7.6 g. of a dark yellow solid, mp 265°–292° C. Formation of the ethylenediamine salt in hot pyridine produces a pure water soluble salt. This salt is dissolved in water and the pure acid is precipitated with dilute acetic acid and recrystallization from dimethylformamide-acetic acid-water to give 1.8 g. (10.1%) of pure 2-n-butyl-11-oxo-11H-pyrido[2,1-b]quinazoline-8-carboxylic acid, mp 250°–253°.

EXAMPLE 29

Preparation of 2-ethyl-11-oxo-11H-pyrido[2,1b-]quinazoline-8-carboxylic acid

This compound was synthesized according to Procedure J above. Yield: 26.4%, mp 313°–315°.

EXAMPLE 30

Preparation of 2-isopropoxy-11-oxo-11H-pyrido[2,1-b]quinazoline-8-carboxylic acid (2-diethylaminoethyl) ester hydrochloride A 9.2 g. portion of diethylaminoethyl chloride hydrochloride was partitioned between 50 ml. of 4 N sodium hydroxide and 100 ml. of ether. The combined ether layers were washed with water and saturated brine, were dried over potassium carbonate and were evaporated to a lightly colored oil. To this oil was added 100 ml. of dry isopropanol and 4.0 g. of pure 2-isopropoxy-11-oxo-11-oxo-11H-pyrido[2,1-b]quinazoline-8-carboxylic acid. The mixture was heated to reflux for 3 hours and cooled. The solids were collected and recrystallized from methanol to give 3.22 g. (57.5%) of 2-isopropoxy-11-oxo-11H-pyrido[2,1-b]quinazoline-8-carboxylic acid (2-diethylaminoethyl)ester hydrochloride, mp 208°–209°.

EXAMPLE 31

Preparation of 8-cyano-2-isopropoxy-11-oxo-11H-pyrido[2,1-b]quinazoline

A mixture of 16.7 g. of 5-isopropoxyanthranilic acid, 10.0 g. of 2-chloro-5-cyanopyridine and 0.01 g. of potassium iodide in 30 ml. of triglyme was heated to a bath temperature of 150° overnight under a stream of argon. On cooling, the mixture was triturated with ethanol and water. A gummy solid was collected, dissolved in hot ethyl acetate, filtered and the filtrate was evaporated to give 8.4 g. of crude product (38% yield). Two recrystallizations of this solid from dimethylformamide-acetic acid-water give pure 8-cyano-2-isopropoxy-11-oxo-11H-pyrido[2,1-b]quinazoline, mp 234°–236°.

EXAMPLE 32

Preparation of 8-hydroxymethyl-2-isopropoxy-11H-pyrido[2,1-b]quinazoline-11-one benzoate A suspension of 1.0 g. of 5-isopropoxyanthranilic acid, 1.1 g. of 6-chloro-3-pyridinemethanol benzoate and 0.01 g. of potassium iodide in 10 ml. of triglyme was heated to 150° overnight under a stream of argon. On cooling, the reaction mixture was dissolved in hot methanol, filtered and evaporated to an orange oil. Chromatographic separation and recrystallization from hexane-dichloromethane yielded 8-hydroxymethyl-2-isopropoxy-11H-pyrido[2,1-b]quinazoline-11-one benzoate, mp 123°–126°.

EXAMPLE 33

Preparation of 2-chrloro-5-(1-hydroxy-1-methylethyl)pyridine

75 Ml. of phosphorous oxychloride and 144 g. of phosphorous pentachloride were added to 100 g. of 6-chloronicotinic acid and intimately mixed. The reaction mixture was slowly heated in an oil bath to 80° over 25 minutes with stirring. The bath temperature was raised to 125° and the solution was stirred and refluxed for 1 hour. After concentration under reduced pressure, anhydrous toluene was added and the solution was concentrated again, finally on the oil pump, to yield 6-chloronicotinoyl chloride as a colorless solid.

This acid chloride was dissolved in 600 ml. of anhydrous ether and added dropwise over 2 hours to a solution of methyl-magnesium iodide prepared from 137 ml. of methyl iodide and 50 g. of magnesium in 700 ml. of anhydrous ether. The reaction mixture was stirred and refluxed for 3 hours. After pouring the cooled reaction mixture carefully into ice and 200 ml. of acetic acid, the aqueous layer was made basic (pH 9) with 425 ml. of 6 N sodium hydroxide. The ether was separated and the aqueous layer was saturated with sodium chloride and extracted four times with ether. After drying the combined extract over anhydrous magnesium sulfate, the extract was concentrated in vacuo to a yellow solid (112 g.). Crystallization from ethyl-acetate-hexane gave 44.5 g., mp 70°–74° of 2-chloro-5-(1-hydroxy-1-methylethyl)pyridine in the first crop. A second crop of 2-chloro-5-(1-hydroxy-1-methylethyl)pyridine (46.7 g., mp 67°–71°) was obtained from ether-hexane.

EXAMPLE 34

Preparation of 2-chloro-5-isopropenylpyridine

A solution of 92.6 g. of 2-chloro-5-(1-hydroxy-1-methylethyl)pyridine, 4.6 g. of p-toluenesulfonic acid monohydrate and 0.9 g. of hydroquinone in 1.5 l. of anhydrous xylene was stirred and refluxed under a Dean-Stark water separator for 4.5 hours. The xylene solution was washed with saturated sodium bicarbonate solution and dried over anhydrous magnesium sulfate. The xylene was removed by distillation (40°–48°/14 mm) through a Claisen head. Distillation of the residual oil through a vigreux column gave 75.6 g. of pure 2-chloro-5-isopropenylpyridine, 110°–114°/8 mm.

EXAMPLE 35

Preparation of 2-chloro-5-isopropylpyridine

A solution of 86.9 g. of 2-chloro-5-isopropenylpyridine and 8.7 g. of platinum oxide in 1 l. of ethanol was shaken at atmospheric pressure in a hydrogen atmosphere for 1 hour 45 minutes. The catalyst was removed by filtration and the filtrate was concentrated in vacuo to yield an oil. Distillation through a vigruex column gave 76.0 g. of pure 2-chloro-5-isopropylpyridine, 105°–109°/8 mm.

EXAMPLE 36

Preparation of
2-bromo-8-isopropyl--
-11-oxo-11H-pyrido[2,1-b]quinazoline

A mixture of 58.5 g. of 5-bromoanthranilic acid, 42.2 g. of 2-chloro-5-isopropylpyridine and 1.7 g of powdered potassium iodide was stirred and heated at 170° under argon for 40 minutes. The bath temperature was lowered to 165° for 4.5 hours and then to 155° for 7 hours. The solid purple cake was triturated with 250 ml. of chloroform, stirred in an ice bath, and filtered to yield the product (34.9 g.) as the hydrochloride. This was suspended in 500 ml. of saturated sodium bicarbonate solution and extracted with methylene chloride. The combined extract was dried over anhydrous magnesium sulfate, stirred briefly with charcoal, filtered and concentrated in vacuo to a yellow solid. Crystallization from methylene chloride-ether gave 21.8 g. of pure 2-bromo-8-isopropyl-11-oxo-11H-pyrido[2,1-b]quinazoline, mp 191°–194°, in two crops.

EXAMPLE 37

Preparation of
8-isopropyl-11-oxo-11H-pyrido[2,1-b]quinazoline-2-
carboxylic acid A mixture of 21.75 g. of 2-bromo-8-isopropyl-11-oxo-11H-pyrido[2,1-b]quinazoline and 5.08 g. of calcium hydroxide in 200 ml. dimethylformamide and 20 ml. of water was placed in a Fischer-Porter bottle under a carbon monoxide atmosphere. Approximately 20 ml. of nickel carbonyl was added and the bottle was pressurized to 20 p.s.i. with carbon monoxide. The reaction mixture was stirred and heated in an oil bath at 120° for 1 hour and after cooling, it was diluted with 1.2 l. of water and 30 ml. of 6 N hydrochloric acid. After stirring overnight, the suspension was filtered and the resultant solid was taken up in dimethylformamide and filtered. The filtrate was concentrated in vacuo on the oil pump to a yellow solid. Water was added along with 5 ml. of acetic acid and the product was removed by filtration to give 18.35 g. of crude product. Crystallization from methanol gave 15.15 g. of pure 8-isopropyl-11-oxo-11H-pyrido[2,1-b]quinazoline-2-carboxylic acid, mp 312°–316°.

EXAMPLE 38

Preparation of
2-cyano-8-isopropyl-11-oxo-11H-pyrido[2,1-b]quinazoline

A solution of 0.412 g. of 2bromo-8-isopropyl-11-oxo-11H-pyrido[2,1-b]quinazoline and 0.233 g. of cuprous cyanide in 5 ml. of 1-methyl-2-pyrrolidinone was stirred and heated at 180° for 10 hours. A solution of 0.52 g. of ferric chloride hexahydrate, 0.13 ml. concentrated hydrochloric acid in 0.8 ml. of water was added and the mixture was heated at 90° for 30 minutes. 25 Ml. of water was added after cooling and the reaction mixture was extracted with chloroform. The extract was washed with 1 N hydrochloric acid, 1 N sodium hydroxide and saturated brine, dried over anhydrous magnesium sulfate and concentrated to a yellow solid which also contained some 1-methyl-2-pyrrolidinone. Ether was added and the product was separated by filtration to give 0.240 g., mp 207°–211°, of 2-cyano-8-isopropyl-11-oxo-11H-pyrido[2,1-b]quinazoline. Preparative tlc gave the pure compound, mp 212°–214°.

EXAMPLE 39

Preparation of
8-isopropyl-11-oxo-11H-pyrido[2,1-b]quinazoline-2-
carboxylic acid A solution of 0.084 g. of 2-cyano-8-isopropyl-11-oxo-11H-pyrido[2,1-b]quinazoline in 1 ml. of acetic acid, 1 ml. of concentrated sulfuric acid and 1 ml. of water was stirred and refluxed for 45 minutes. The solution was concentrated on the oil pump to a small volume. After cooling in an ice bath, 50 ml. of saturated sodium bicarbonate was added carefully. The mixture was then acidified with acetic acid and the resultant solid was filtered and washed with water to yield 0.063 g., mp 313°–314°, of pure 8-isopropyl-11-oxo-11H-pyrido[2,1-b]quinazoline-2-carboxylic acid.

EXAMPLE 40

Preparation of
8-isopropyl-11-oxo-11H-pyrido[2,1-b]quinazoline-2-
carboxylic acid (2-diethylaminoethyl)ester
hydrochloride 0.86 G. of 2-diethylaminoethyl chloride was dissolved in 5 ml. of water and 5 ml. of saturated sodium bicarbonate solution was added and stirred in an ice bath for 5 minutes. This solution was extracted with ether, the extract was dried over anhydrous magnesium sulfate and concentrated in vacuo to given the base as a colorless oil (0.41 g.). This was added to 0.423 g. of 8-isopropyl-11-oxo-11H-pyrido[2,1-b]quinazoline-2-carboxylic acid in 10 ml. of anhydrous isopropanol and the reaction mixture was stirred and refluxed for 3 hours. After cooling to room temperature, the product was removed by filtration and purified by crystallization from isopropanol and then from methylene chloride-ether to give 0.25 g. of pure 8-isopropyl-11-oxo-11H-pyrido[2,1-b]quinazoline-2-carboxylic acid (2-diethylaminoethyl)ester hydrochloride, mp 238°–239°.

EXAMPLE 41

Preparation of 4-isopropyl-isonitrosoacetanilide

To a stirred solution of 1480 g. of sodium sulfate decahydrate dissolved in 1.8 l. of water were added the following solutions: 100 g. of p-isopropylaniline dissolved in 440 ml. of water and 66 ml. of concentrated hydrochloric acid, 244 g. of chloral hydrate dissolved in 2.6 l. of 90% aqueous ethanol, and 162 g. of hydroxylamine hydrochloride dissolved in 700 ml. of water. This reaction mixture was refluxed for 12 hours, cooled to room temperature and extracted with 1.8 l. of dichloromethane. The organic layer was separated and evaporated to a dark oil. This oil was partitioned between 1.0 l. of 10% sodium hydroxide solution and 500 ml. of ether. The aqueous layer was separated and washed with two 500 ml. portions of ether. The aqueous layer was then acidified with concentrated hydrochloric acid and extracted with three 500 ml. portions of ether. The combined ether extracts were dried over anhydrous sodium sulfate, filtered through Celite and evaporated to dryness to give 160 g. of 4-isopropyl-isonitrosoacetanilide. This crude product was recrystallized from 250 ml. of benzene to yield 46.6 g. of product, mp 126°–130°.

EXAMPLE 42

Preparation of 5-isopropylanthranilic acid

460 Ml. of concentrated sulfuric acid was stirred and heated to 70°. 46.6 G. of 4-isopropylisonitrosoacetanilide was then added at such a rate so as to maintain the temperature of the reaction mixture between 70°–80°. Water cooling was applied as necessary. Upon completion of the addition, the temperature of the mixture was maintained at 80° for 30 minutes. The reaction mixture was cooled to room temperature and poured onto 4 l. of crushed ice. The resulting suspension was stirred for 15 minutes and the precipitated 5-isopropylisatin was filtered. The solid was washed with water, collected and dissolved in 460 ml. of 1 N sodium hydroxide solution. The mixture was filtered to remove insolubles and the filtrate was treated with 30% peroxide until a positive starch iodide test was obtained.

The above reaction mixture was cooled in an ice bath and acidified with 6 N hydrochloric acid solution until a pH of approximately 4 was obtained. The precipitated product was collected and dried to give 28.0 g. of 5-isopropylanthranilic acid, mp 90°–96°. This product was of sufficient purity for further use.

EXAMPLE 43

Preparation of 2-isopropyl-11-oxo-11H-pyrido[2,1-b]quinazoline-8-carboxylic acid A suspension of 6.0 g. of 5-isopropylanthranilic acid, 5.4 g. of 6-chloronicotinic acid and 0.05 g. of potassium iodide in 10 ml. of triglyme was heated overnight (bath temperature 150°) under a stream of argon. On cooling, the mixture was triturated with ethanol and water and filtered to give 5.89 g. of crude product, mp 280°–287°. This material was dissolved in hot pyridine and treated with ethylenediamine to give the corresponding salt which was collected by filtration. This salt was dissolved in water and the pure acid was precipitated with dilute acetic acid. Recrystallization from dimethylformamide-acetic acid-water gave 2.5 g. (26.6%) of 2-isopropyl-11-oxo-11H-pyrido[2,1-b]quinazoline-8-carboxylic acid, mp 314°–316°.

EXAMPLE 44

Preparation of 2-isopropyl-11-oxo-11H-pyrido[2,1-b]quinazoline-8-carboxylic acid (2-diethylaminoethyl)ester hydrochloride 5.8 G. of diethylaminoethylchloride hydrochloride was partitioned between 100 ml. of 2 N sodium hydroxide and 100 ml. of ether. The ether layer was separated, washed with water and saturated brine, dried (potassium carbonate) and evaporated to a light colored oil. To this oil was added 200 ml. of isopropanol and 2.4 g. of pure 2-isopropyl-11-oxo-11H-pyrido[2,1-b]quinazoline-8-carboxylic acid. The mixture was refluxed for 3 hours and cooled. The solids were collected and recrystallized from methanol to give 1.87 g. (53.4%) of 2-isopropyl-11-oxo-11H-pyrido[2,1-b]quinazoline-8-carboxylic acid (2-diethylaminoethyl)ester hydrochloride, mp 220°–222°.

EXAMPLE 45

Preparation of 5-hydroxy-2-nitrobenzoic acid

A mixture of 5.0 l. of water, 800 g. of sodium hydroxide and 504 g. of 5-chloro-2-nitrobenzoic acid was refluxed for 24 hours. The solution was cooled and acidified with 1.75 l. of concentrated hydrochloric acid. The acidic aqueous mixture was extracted three times with 1.5 l. of ether. The combined ether extracts were dried over anhydrous magnesium sulfate, filtered through Celite and evaporated to a light yellow solid (473 g.). This material was recrystallized from ether-petroleum ether to yield 298 g. of 5-hydroxy-2-nitrobenzoic acid, mp 167°–169° (65.2%).

EXAMPLE 46

Preparation of 5-isopropoxy-2-nitrobenzoic acid, isopropyl ester

A mixture of 55.3 g. of 5-hydroxy-2-nitrobenzoic acid, 450 ml. of dimethylformamide and 93.9 g. of anhydrous potassium carbonate was stirred at room temperature for 10 minutes. 100 Ml. of isopropylbromide was then added and the mixture was stirred and heated to 100° for five hours. The reaction mixture was then cooled and diluted with ice water. The pH of the mixture was adjusted to ~8 with 4 N sodium hydroxide solution. The mixture was then extracted three times with 500 ml. of ether. The combined ether extracts were washed with 500 ml. of saturated brine, dried over anhydrous potassium carbonate, filtered through Celite and evaporated to a yellow oil which crystallized on cooling to yield 74.0 g. of 5-isopropoxy-2-nitrobenzoic acid, isopropyl ester, mp 45°–50° (91.7%). This material may be distilled under high vacuum to give pure product, mp 51°–52°.

EXAMPLE 47

Preparation of 5-isopropoxy-anthranilic acid 74.0 G. of 5-isopropoxy-2-nitrobenzoic acid, isopropyl ester was dissolved in 650 ml. of ethanol and 145 ml. of 4 N sodium hydroxide solution. This solution was allowed to stir at room temperature for 16 hours. The reaction mixture was diluted with 2.0 l. of water and washed three times with 1 l. of dichloromethane. The aqueous layer was then acidified to pH<2 with concentrated hydrochloric acid and extracted three times with 1.0 l. of ether. The combined ether extracts were washed with 1.0 l. of saturated brine, dried over anhydrous sodium sulfate, filtered through Celite and evaporated to an orange oil (65.9 g.) which solidified on cooling, mp 129°–131°. The above solid was dissolved in 1.0 l. of ethyl acetate and hydrogenated, using 3.1 g. of 10% palladium on carbon as catalyst. When hydrogen uptake had ceased, the catalyst was removed by filtration and the filtrate was evaporated to a yellow solid, 49.5 g. (mp 120°–122°).

EXAMPLE 48

Preparation of 2-isopropoxy-11-oxo-11H-pyrido[2,1-b]quinazoline-8-carboxylic acid A mixture of 23.2 g. of 5-isopropoxyanthranilic acid, 15.7 g. of 6-chloronicotinic acid, 0.1 g. of potassium iodide and 50 ml. of triglyme was heated to 150° under a constant stream of argon for 16 hours. The reaction mixture was cooled, diluted with about 50 ml. of ethanol and filtered to give 18.9 g. of crude product, mp 256°-267°. This material was dissolved in about 50 ml. of hot pyridine. To the boiling solution was added 4.8 ml. of ethylenediamine. This mixture was allowed to cool and the crystals which had precipitated were filtered, washed with pyridine, pressed dry and dissolved in 50 ml. of water. This aqueous solution was stirred and carefully acidified with dilute acetic acid. The crystals which precipitated were collected, washed with water, ethanol and ether and dried to yield 9.8 g. of 2-isopropoxy-11-oxo-11H-pyrido[2,1-b]quinazoline-8carboxylic acid, mp 278°-280°.

EXAMPLE 49

Preparation of 2-methylthio-11-oxo-11H-pyrido[2,1-b]quinazoline-8carboxylic acid A stirred intimate mixture of 50 g. of methyl-5-methylmercapto anthranilate hydrochloride, 34.7 g. of 6-chloronicotinic acid and 0.1 g. of potassium iodide was immersed in an oil bath preheated to 150°. 40 Ml. of triglyme was carefully added to the mixture. The reaction mixture was heated to 175° for 16 hours under a slow stream of argon. The reaction was cooled and the solid residue was dissolved in hot dimethylformamide and glacial acetic acid, filtered and cooled. The precipitated product was collected, washed with ethanol and dried to yield 31.3 g. (51%) of 2-methylthio-11-oxo-11H-pyrido[2,1-b]quinazoline-8-carboxylic acid, mp 303°-320°.

The crude material (10 g.) was dissolved in 150 ml. of hot pyridine. To this hot solution was added about 1.25 ml. of ethylenediamine. The resulting mixture was stirred as it cooled. The resulting crystals were collected, pressed dry and dissolved in water. This solution was carefully acidified with dilute acetic acid and the precipitated product was filtered and dried to yield 1.7 g. of purified product, mp 337°.

EXAMPLE 50

Preparation of 2-methylthio-11-oxo-11H-pyrido[2,1-b]quinazoline-8-carboxylic acid (2-diethylaminoethyl)ester hydrochloride 2.5 G. of N,N-diethylaminoethyl chloride hydrochloride was partitioned between 50 ml. of ether and 50 ml. of 2 N sodium hydroxide solution. The aqueous layer was extracted twice with 50 ml. of ether and the combined ether layers were washed with 50 ml. of water and 50 ml. of saturated brine. The organic phase was then dried over anhydrous potassium carbonate, filtered through Celite and evaporated to a light colored oil (1.61 g.). This oil was dissolved in 35 ml. of isopropanol and to this stirred solution was added 1.15 g. of purified 2-methylthio-11-oxo-11H-pyrido[2,1-b]quinazoline-8-carboxylic acid. The resulting reaction mixture was refluxed for 4 hours and cooled. The crystalline product was collected by filtration and recrystallized from methanol to yield 1.16 g. (92%) of the desired 2-methylthio-11-oxo-11H-pyrido[2,1-b]quinazoline-8-carboxylic acid (2-diethylaminoethyl)ester as its hydrochloride salt, mp 236°-238°.

EXAMPLE 51

Preparation of 4-isopropyl-2-bromo acetanilide

A solution of 50 g. of 4-isopropylaniline in 160 ml. of glacial acetic acid was stirred and refluxed for 2 hours. The solution was then cooled to 45° and dropwise addition of 60 g. of bromine was begun. The addition was continued at such a rate so as to maintain the temperature of the reaction solution below 55°. Upon completion of the addition, the reaction was allowed to stir for 1 hour. The dark liquid was then poured onto 2 l. of crushed ice with stirring. The resulting suspension was allowed to stir for 10 minutes as 5.0 g. of sodium bisulfite was added. This suspension was stirred until the bromine color had been discharged. The solid was then filtered, washed with water and air dried overnight.

The damp solid (115 g.) was recrystallized from 1.0 l. of 50% aqueous ethanol to give 64.4 g. (68.2%) of 4-isopropyl-2-bromo acetanilide, mp 122°-126°.

EXAMPLE 52

Preparation of 2-cyano-4-isopropylacetanilide

A solution of 1.0075 g. of 2-bromo-4-isopropylacetanilide and 0.7308 g. of cuprous cyanide in 10 ml. of N-methylpyrrolidinone was heated and stirred at 180° for 7 hours. The reaction mixture was poured into 1 ml. of ethylenediamine in 50 ml. of water and stirred vigorously for 5 minutes. After extraction with chloroform, the extract was washed with 10% sodium cyanide solution, washed with water, dried over magnesium sulfate and concentrated in vacuo to an oil. Residual N-methylpyrrolidinone was removed by distillation (bp 33°-37°/0.1 mm) and the viscous residue crystallized on cooling. Recrystallization from ether-hexane gave 2-cyano-4-isopropylacetanilide (0.5920 g., mp 98°-100°).

EXAMPLE 53

Preparation of 5-isopropylanthranilic acid

A solution of 0.4870 g. of 2-cyano-4-isopropylacetanilide in 5 ml. of acetic acid and 10 ml. of 50% sulfuric acid was refluxed for 2½ hours. The solution was concentrated on the oil pump to a small volume. Water (5 ml.) was added and the pH was adjusted to 4 by the addition of 6 N sodium hydroxide. After cooling, the precipitate was filtered and dried to give 0.3426 g. of material. Recrystallization from ligroine gave 5-isopropylanthranilic acid (0.3010 g., mp 75°-80°).

EXAMPLE 54

Preparation of 2-bromo-4-cyclopropylacetanilide

To 15.20 g. of 4-cyclopropylacetanilide[1] and 10.45 g. of acetamide dissolved in 1 liter of chloroform and cooled at −25° was added a solution of 13.8 g. of bromine in 300 ml. of chloroform dropwise with stirring over 2 hours. The reaction mixture was stirred at −25° for 70 hours and then allowed to warm to 5°. After filtration to remove the precipitate, the filtrate was concentrated in vacuo. The crude product was dissolved in ethyl acetate, dried over anhydrous sodium sulfate and concentrated in vacuo to an orange solid. This was chromatographed on 1.2 kg. of silica gel and eluted with 40% ethyl acetate-toluene. The combined pure fractions were concentrated in vacuo to yield 11.22 g., mp 108.5°-110°, of pure 2-bromo-4-cyclopropylacetanilide.

[1] R. C. Hahn et al., J. Amer. Chem. Soc., 90, 3404 (1968).

EXAMPLE 55

Preparation of 2-cyano-4-cyclopropylacetanilide

A solution of 11.22 g. of 2-bromo-4-cyclopropylacetanilide in 500 ml. of anhydrous dimethylformamide and 8.96 g. of cuprous cyanide was stirred and refluxed for 3 hours. After cooling to 25°, the dimethylformamide was removed in vacuo. The residue was stirred with 15 ml. of ethylene diamine in 500 ml. of water for 30 minutes and then extracted with ethyl acetate. The extract was dried over sodium sulfate and concentrated in vacuo to a solid. Crystallization from ethyl acetate-hexane gave 6.45 g., mp 140°–141°, of pure 2-cyano-4-cyclopropylacetanilide.

EXAMPLE 56

Preparation of 5-cyclopropylanthranilic acid

To a solution of 6.30 g. of 2-cyano-4-cyclopropylacetanilide in 60 ml. of ethylene glycol-60 ml. of water was added 8.86 g. of potassium hydroxide. The reaction mixture was stirred and refluxed for 19 hours. After cooling, 1 liter of water was added. The solid which precipitated was removed by filtration and the filtrate was extracted several times with ethyl acetate. The basic aqueous layer was acidified to a pH of 3 with acetic acid and extracted with ethyl acetate. The dried (over sodium sulfate) extract was concentrated in vacuo to a solid. Crystallization from ether-hexane gave 2.31 g., mp 157.5°–158.5°, of pure 5-cyclopropylanthranilic acid.

EXAMPLE 57

Preparation of 2-cyclopropyl-11-oxo-11H-pyrido[2,1-b]quinazoline-8-carboxylic acid A solution of 2.12 g. of 5-cyclopropylanthranilic acid and 1.89 g. of 6-chloronicotinic acid in 20 ml. of toluene was boiled to remove the toluene. The resultant solid mixture was heated at 150° for 25 minutes. After cooling, the solid residue was triturated with ether and filtered. The resultant solid was crystallized from acetic acid and then from ethanol to give 0.275 g., mp 316°–318°, of pure 2-cyclopropyl-11-oxo-11H-pyrido[2,1-b]quinazoline-8-carboxylic acid.

The acid is reacted with 2-diethylaminoethyl chloride in isopropanol, as described in Example 44, to give 2-cyclopropyl-11-oxo-11H-pyrido[2,1-b]quinazoline-8-carboxylic acid (2-diethylaminoethyl) ester hydrochloride.

EXAMPLE 58

Preparation of 8-acetyl-2-bromo-11-oxo-11H-pyrido[2,1-b]quinazoline

A suspension of 15.50 g. of 5-bromoanthranilic acid, 11.9 g. of 2-chloro-5-acetylpyridine and 0.50 g. of potassium iodide in 20 ml. of triglyme was heated at a bath temperature at 150° under an atmosphere of argon for 7 hours. 40 Ml. of methanol was added and the mixture was stirred in an ice bath for 30 minutes and filtered. The product was suspended in 500 ml. of saturated sodium bicarbonate solution and extracted with chloroform. The extract was concentrated to a yellow solid (9.70 g.) which was crystallized and recrystallized from methylene chloride-ether to give 5.10 g. (mp 221°–224°) of pure 8-acetyl-2-bromo-11-oxo-11H-pyrido[2,1-b]quinazoline.

EXAMPLE 59

Preparation of 8-acetyl-11-oxo-11H-pyrido[2,1-b]quinazoline-2-carboxylic acid

A mixture of 1.0 g. of 8-acetyl-2-bromo-11-oxo-11H-pyrido[2,1-b]quinazoline and 0.234 g. of calcium hydroxide in 25 ml. of dimethylformamide and 2.5 ml. of water was placed in a Fischer-Porter bottle under a carbon monoxide atmosphere. Approximately 2 ml. of nickel carbonyl was added and the bottle was pressurized to 20 p.s.i. with carbon monoxide. The reaction mixture was stirred and heated in an oil bath at 120° for 19 hours and after cooling, it was diluted with 200 ml. of water and 4 ml. of 6 N hydrochloric acid. After stirring overnight, the solid was filtered and refluxed in 1 l. of methanol and the solution was filtered. The filtrate was concentrated on the steam bath to a small volume, cooled and filtered to give 0.33 g., mp 305°–309°, of pure 8-acetyl-11-oxo-11H-pyrido[2,1-b]quinazoline-2-carboxylic acid.

EXAMPLE 60

| Capsule Formulation | | |
|---|---|---|
| | mg/capsule | |
| | 10 mg | 20 mg |
| 2-Methoxy-11-oxo-11H-pyrido[2,1-b]-quinazoline-8-carboxylic acid | 10.0 | 20.0 |
| Lactose | 215.0 | 205.0 |
| Cornstarch | 60.0 | 60.0 |
| Magnesium Stearate | 3.0 | 3.0 |
| Talc | 12.0 | 12.0 |
| Total | 300 mg. | 300 mg. |

PROCEDURE

Mix 2-methoxy-11-oxo-11H-pyrido[2,1-b]quinazoline-8-carboxylic acid, lactose and cornstarch in a suitable mixer. Mill through suitable mill. Mix with magnesium stearate and talc and fill on capsule machine.

EXAMPLE 61

| Tablet Formulation | | |
|---|---|---|
| | mg/tablet | |
| | 10 mg | 20 mg. |
| 2-Methoxy-11-oxo-11H-pyrido[2,1-b]-quinazoline-8-carboxylic acid | 10.0 | 20.0 |
| Lactose | 182.0 | 172.0 |
| Microcrystalline Cellulose | 60.0 | 60.0 |
| Modified Starch | 15.0 | 15.0 |
| Cornstarch | 30.0 | 0.0 |
| Magnesium Stearate | 3.0 | 3.0 |
| Total | 300 mg | 300 mg. |

PROCEDURE

Mix 2-methoxy-11-oxo-11H-pyrido[2,1-b]quinazoline-8-carboxylic acid, lactose, microcrystalline cellulose, modified starch and cornstarch in a suitable mixer for 1 to 15 minutes. Then, add magnesium stearate and mix for 5 minutes. Compress on a suitable press.

EXAMPLE 62

| Wet Granulation Tablet Formulation | | |
|---|---|---|
| | mg/tablet | |
| | 10 mg | 20 mg |
| 2-Methoxy-11-oxo-11H-pyrido[2,1-b]- quinazoline-8-carboxylic acid | 10.0 | 20.0 |
| Lactose | 264.0 | 254.0 |
| Pregelatinized Starch | 17.5 | 17.5 |
| Cornstarch | 35.0 | 35.0 |
| Modified Starch | 17.5 | 17.5 |
| Magnesium Stearate | 6.0 | 6.0 |
| Total | 350 mg. | 350 mg. |

PROCEDURE

Mix 2-methoxy-11-oxo-11H-pyrido[2,1-b]quinazoline-8-carboxylic acid, lactose and pregelatinized starch in a suitable mixer. Mill through suitable mill. Mix with modified starch and magnesium stearate and fill on capsule machine.

We claim:

1. A compound of the formula

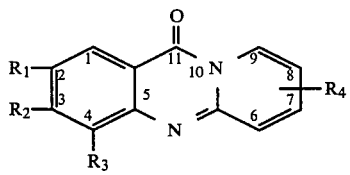

wherein $R_1$, $R_2$ and $R_3$, independently, are hydrogen, isopropyl, lower alkoxy, lower alkylthio, cyclopropyl, or cyclobutyl; and $R_4$ is cyano, hydroxy-lower alkyl, lower alkanoyloxy-lower alkyl, benzoyloxy-lower alkyl or a radical of the formula

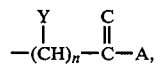

wherein A is lower alkyl, hydroxy, lower alkoxy, di-$(C_1-C_7)$alkylamino-$(C_2-C_7)$-alkoxy, pivaloyloxymethoxy, or a radical of the formula

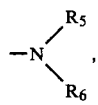

wherein $R_5$ and $R_6$, independently, are hydrogen, lower alkyl or di-$(C_1-C_7)$alkylamino-$(C_2-C_7)$alkyl, Y is hydrogen or methyl, and n is 0 or 1; provided that only one of $R_1$, $R_2$ or $R_3$ is other than hydrogen and that $R_4$ is present only in position 6, 7 or 8, or a pharmaceutically acceptable acid addition salt thereof, or when A is hydroxy, also a salt thereof with a pharmaceutically acceptable base.

2. A compound, in accordance with claim 1, of the formula

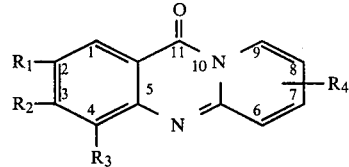

wherein $R_1$, $R_2$ and $R_3$, independently, are hydrogen, isopropyl, lower alkoxy, cyclopropyl, or cyclobutyl; and $R_4$ is cyano, hydroxy-lower alkyl, lower alkanoyloxy-lower alkyl, benzoyloxy-lower alkyl or a radical of the formula

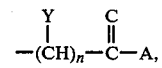

wherein A is lower alkyl, hydroxy, lower alkoxy, di-$(C_1-C_7)$alkylamino-$(C_2-C_7)$-alkoxy, pivaloyloxymethoxy, or a radical of the formula

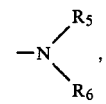

wherein $R_5$ and $R_6$, independently, are hydrogen, lower alkyl or di-$(C_1-C_7)$alkylamino-$(C_2-C_7)$alkyl, Y is hydrogen or methyl, and n is 0 or 1; provided that only one of $R_1$, $R_2$ or $R_3$ is other than hydrogen and that $R_4$ is present only in position 8, or a pharmaceutically acceptable acid addition salt thereof, or when A is hydroxy, also a salt thereof with a pharmaceutically acceptable base.

3. A compound of the formula

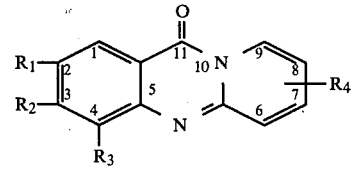

wherein $R_1$, $R_2$ and $R_3$, independently, are hydrogen, lower alkoxy, lower alkylthio, cyclopropyl, or cyclobutyl; and $R_4$ is 5-tetrazolyl; provided that only one of $R_1$, $R_2$ or $R_3$ is other than hydrogen and that $R_4$ is present only in position 6, 7 or 8, or a pharmaceutically acceptable acid addition salt thereof.

4. A compound in accordance with claim 2, wherein $R_4$ is a substituent in position 8.

5. A compound in accordance with claim 4, wherein $R_4$ is

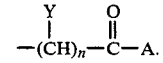

6. A compound in accordance with claim 5, wherein n is 0.

7. A compound in accordance with claim 6, wherein A is hydroxy.

8. A compound in accordance with claim 6, wherein A is di-$(C_1-C_7)$alkylamino-$(C_2-C_7)$alkoxy.

9. A compound in accordance with claim 4, wherein $R_4$ is hydroxyalkyl.

10. A compound in accordance with claim 7, wherein $R_2$ and $R_3$ are hydrogen.

11. A compound in accordance with claim 7, wherein $R_1$ and $R_2$ are hydrogen.

12. A compound in accordance with claim 10, wherein $R_1$ is lower alkoxy.

13. A compound in accordance with claim 1, wherein $R_1$ is lower alkylthio.

14. A compound in accordance with claim 10, wherein $R_1$ is isopropyl.

15. A compound in accordance with claim 3, 2-methoxy-11-oxo-11H-8-(1H-tetrazol-5-yl)pyrido[2,1-b]quinazoline.

16. A compound in accordance with claim 2, 2-methoxy-11-oxo-11H-pyrido[2,1-b]quinazoline-8-carboxylic acid (2-diethylaminoethyl) ester.

17. A compound in accordance with claim 2, 8-hydroxymethyl-2-methoxy-11H-pyrido[2,1-b]quinazolin-11-one hydrochloride.

18. A compound in accordance with claim 2, 2-isopropoxy-11-oxo-11H-pyrido[2,1-b]quinazoline-8-carboxylic acid.

19. A compound in accordance with claim 13, 2-methylthio-11-oxo-11H-pyrido[2,1-b]quinazoline-8-carboxylic acid.

20. A compound in accordance with claim 2, 2,4-dimethoxy-11-oxo-11H-pyrido[2,1-b]quinazoline-8-carboxylic acid.

21. A compound in accordance with claim 2, 2-isopropyl-11-oxo-11H-pyrido[2,1-b]quinazoline-8-carboxylic acid (2-diethylaminoethyl) ester.

22. A compound in accordance with claim 2, 2-isopropyl-11-oxo-11H-pyrido[2,1-b]quinazoline-8-carboxylic acid.

23. A compound in accordance with claim 2, 4-methoxy-11-oxo-11H-pyrido[2,1-b]quinazoline-8-carboxylic acid.

24. A compound in accordance with claim 2, 2-methoxy-11-oxo-11H-pyrido[2,1-b]quinazoline-8-carboxylic acid sodium salt, monohydrate.

25. A compound in accordance with claim 2, 2-methoxy-11-oxo-11H-pyrido[2,1-b]quinazoline-8-carboxylic acid.

26. A compound in accordance with claim 2, 2-methoxy-11-oxo-11H-pyrido[2,1-b]quinazoline-8-acetic acid.

27. A compound in accordance with claim 2, 2-cyclopropyl-11-oxo-11H-pyrido[2,1-b]quinazoline-2-carboxylic acid.

28. A compound in accordance with claim 2, 2-cyclopropyl-11-oxo-11H-pyrido-[2,1-b]quinazoline-2-carboxylic acid (2-diethylaminoethyl) ester.

29. The compound, 8-isopropyl-11-oxo-11H-pyrido[2,1-b]quinazoline-2-carboxylic acid.

30. The compound, 8-isopropyl-11-oxo-11H-pyrido-[2,1-b]quinazoline-2-carboxylic acid (2-diethylaminoethyl) ester.

31. A compound in accordance with claim 2, 2-methoxy-11-oxo-11H-pyrido[2,1-b]quinazoline-8-carbonamide.

32. A compound in accordance with claim 2, 2-methoxy-11-oxo-11H-pyrido[2,1-b]quinazoline-8-carbonitrile.

33. Method of inhibiting allergic reactions which comprises administering an effective amount of the compound of the formula

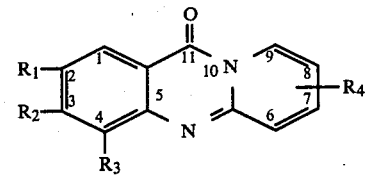

wherein $R_1$, $R_2$ and $R_3$, independently, are hydrogen, isopropyl, lower alkoxy, cyclopropyl, or cyclobutyl; and $R_4$ is cyano, hydroxy-lower alkyl, lower alkanoyloxy-lower alkyl, benzoyloxy-lower alkyl or a radical of the formula

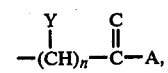

wherein A is lower alkyl, hydroxy, lower alkoxy, di-$(C_1-C_7)$alkylamino-$(C_2-C_7)$-alkoxy, pivaloyloxymethoxy, or a radical of the formula

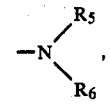

wherein $R_5$ and $R_6$, independently, are hydrogen, lower alkyl or di-$(C_1-C_7)$alkylamino-$(C_2-C_7)$alkyl, Y is hydrogen or methyl, and n is 0 or 1; provided that only one of $R_1$, $R_2$ or $R_3$ is other than hydrogen and that $R_4$ is present only in position 8, or a pharmaceutically acceptable acid addition salt thereof, or when A is hydroxy, also a salt thereof with a pharmaceutically acceptable base.

34. Method of inhibiting allergic reactions which comprises administering an effective amount of the compound of the formula

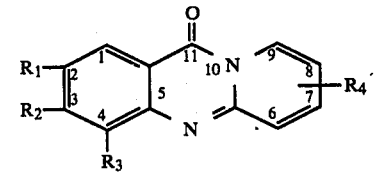

wherein $R_1$, $R_2$ and $R_3$, independently, are hydrogen, lower alkoxy, cyclopropyl, or cyclobutyl; and $R_4$ is 5-tetrazolyl; provided that only one of $R_1$, $R_2$ or $R_3$ is other than hydrogen and that $R_4$ is present only in position 8, or a pharmaceutically acceptable acid addition salt thereof.

35. A method of inhibiting allergic reactions which comprises administering an effective amount of a compound selected from the group consisting of 8-isopropyl-11-oxo-11H-pyrido[2,1-b]quinazoline-2-carboxylic acid and a pharmaceutically acceptable acid addition salt thereof, and 8-isopropyl-11-oxo-11H-pyrido-[2,1-b]quinazoline-2-carboxylic acid (2-diethylaminoethyl) ester.

* * * * *